United States Patent
Truesdale et al.

(10) Patent No.: US 6,307,054 B1
(45) Date of Patent: Oct. 23, 2001

(54) PROCESS FOR PREPARING 2,4-DIHYDROXYPYRIDINE AND 2,4-DIHYDROXY-3-NITROPYRIDINE

(75) Inventors: Larry K. Truesdale, San Diego, CA (US); James P. Sherbine, Voorhees, NJ (US); Benoit J. Vanasse, Collegeville, PA (US)

(73) Assignee: Aventis Pharmaceuticals Products Inc., Bridgewater, NJ (US)

( * ) Notice: Subject to any disclaimer, the term of this patent is extended or adjusted under 35 U.S.C. 154(b) by 0 days.

(21) Appl. No.: 09/108,622

(22) Filed: Jul. 1, 1998

Related U.S. Application Data

(63) Continuation of application No. PCT/US96/20768, filed on Dec. 23, 1996.
(60) Provisional application No. 60/009,492, filed on Jan. 2, 1996.

(51) Int. Cl.[7] ............ C07D 213/69; C07D 213/73; C07D 213/78
(52) U.S. Cl. ................................ 546/296; 546/297
(58) Field of Search ...................... 546/297, 296

(56) References Cited

U.S. PATENT DOCUMENTS

| | | | |
|---|---|---|---|
| 3,547,935 | * 12/1970 | Diehl et al. | 546/297 |
| 3,682,929 | 8/1972 | Siggel et al. | |
| 4,529,800 | * 7/1985 | Orth et al. | 546/297 |

FOREIGN PATENT DOCUMENTS 6-220019   8/1994   (JP) .

OTHER PUBLICATIONS

Journal Of Medicinal Chemistry, vol. 16, No. 3, pp. 294–97, 1973.*
Shone et al., Journal of Heterocyclic Chemistry, vol. 12, No. 2, pp. 389–90, 1975.*
Kogl et al., Recuel, vol. 67, pp. 29–44.*
Kogl et al., Recueil, 67, 29–44 (1948).

* cited by examiner

Primary Examiner—Alan L. Rotman
(74) Attorney, Agent, or Firm—Irving Newman

(57) ABSTRACT

The present invention is directed to a process for preparing 2,4-dihydroxy-pyridine comprising heating a compound of the formula A

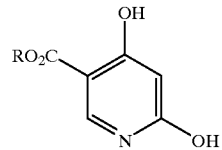

(A)

wherein R is H, alkyl or aralkyl and phosphoric acid where the ratio of phosphoric acid to water is not less than about 27 to 1 weight %. The invention is also directed to a process for preparing 2,4-dihydroxy-3-nitropyridine comprising reacting 2,4-dihydroxypyridine with nitric acid.

The processes of the present invention prepare intermediates which are useful in preparing compounds which are useful for treating cardiovascular disease marked by hypertension or myocardial ischemia, ameliorating ischenic injury or myocardial infarct size, or treating hyperlipidemia or hypercholesterolemia.

4 Claims, No Drawings

PROCESS FOR PREPARING 2,4-DIHYDROXYPYRIDINE AND 2,4-DIHYDROXY-3-NITROPYRIDINE

CROSS-REFERENCE

This application is a continuation of PCT/US96/20,768 filed Dec. 23, 1996, which claims benefit of Provisional Application No. 60/009,492 filed Jan. 2, 1996.

BACKGROUND OF THE INVENTION

1. Field of the Invention

This invention relates to processes for preparing 2,4-dihydroxypyridine and 2,4-dihydroxy-3-nitropyridine which compounds are intermediates that are useful in preparing adenosine compounds and analogs thereof which are useful in treating hypertension and myocardial ischemia, as cardioprotective agents which ameliorate ischemic injury or myocardial infarct size consequent to myocardial ischemia, and as antilipolytic agents which reduce plasma lipid levels, serum triglyceride levels, and plasma cholesterol levels.

Hypertension

Hypertension, a condition of elevated blood pressure, affects a substantial number of the human population. Consequences of persistent hypertension include vascular damage to the ocular, renal, cardiac and cerebral systems, and the risk of these complications increases as blood pressure increases. Basic factors controlling blood pressure are cardiac output and peripheral vascular resistance, with the latter being the predominant common mechanism which is controlled by various influences. The sympathetic nervous system regulates peripheral vascular resistance through direct effects on alpha- and beta-adrenergic receptors as well as through indirect effects on renin release. Drug therapy is aimed at specific components of these blood pressure regulatory systems, with different mechanisms of action defining the several drug classes including diuretics, beta-adrenergic receptor antagonists (beta-blockers), angiotensin-converting enzyme (ACE) inhibitors, and calcium channel antagonists.

Thiazide-type diuretics are used in hypertension to reduce peripheral vascular resistance through their effects on sodium and water excretion. This class of drugs includes hydrochlorothiazide, chlorothiazide, methyclothiazide, and cyclothiazide, as well as related agents indapamide, metolazone, and chlorthalidone. Although the beta-blocker mechanism of action was once believed to be blockade of the $beta_1$-adrenergic receptor subtype in the heart to reduce heart rate and cardiac output, more recent beta-blockers with intrinsic sympathomimetic activity (ISA), including pindolol, acebutolol, penbutolol, and carteolol, are as effective as non-ISA beta-blockers, causing less reduction in heart rate and cardiac output. Other postulated mechanisms for these drugs include inhibition of renin release, a central effect, and an effect at pre-synaptic beta-adrenergic receptors resulting in inhibition of norepinephrine release. Cardioselective beta-blockers metoprolol (Lopressor-Geigy), acebutolol (Sectral-Wyeth), and atenolol (Tenormin-ICI), at low doses, have a greater effect on $beta_1$-adrenergic receptors than on $beta_2$-adrenergic receptor subtypes located in the bronchi and blood vessels. Nonselective beta-blockers act on both beta-adrenergic receptor subtypes and include propranolol (Inderal-Ayerst), timolol (Blocadren-Merck), nadolol (Corgard-Squibb), pindolol (Visken-Sandoz), penbutolol (Levatol-Hoechst-Roussel), and carteolol (Cartrol-Abbott). Adverse effects of beta-blockers include asymptomatic bradycardia exacerbation of congestive heart failure, gastrointestinal disturbances, increased airway resistance, masked symptoms of hypoglycemia, and depression. They may cause elevation of serum triglycerides and may lower high-density lipoprotein cholesterol.

ACE inhibitors prevent the formation of angiotensin II and inhibit breakdown of bradykinin. Angiotensin II is a potent vasoconstrictor and also stimulates the secretion of aldosterone. By producing blockade of the renin-angiotensin-aldosterone system, these agents decrease peripheral vascular resistance, as well as sodium and water retention. In addition, ACE inhibitors increase levels of bradykinin and prostaglandins, endogenous vasodilators. Captopril (Capoten-Squibb) and Enalapril (Vasotec-Merck) are the leading ACE inhibitors. Adverse effects of the ACE inhibitors include rash, taste disturbance, proteinuria and neutropenia.

The calcium channel antagonists reduce the influx of calcium into vascular smooth muscle cells and produce systemic vasodilation, resulting in their antihypertensive effect. Other effects of calcium channel antagonists include interference with action of angiotensin II and $alpha_2$-adrenergic receptor blockade, which may add to their antihypertensive effects. Calcium channel antagonists do not have the adverse metabolic and pharmacological effects of thiazides or beta-blockers and may therefore be useful in patients with diabetes, peripheral vascular disease, or chronic obstructive pulmonary disease. Two calcium channel antagonists, Verapamil and diltiazem, have serious adverse cardiovascular effects on atrioventricular cardiac conduction in patients with preexisting conduction abnormalities, and they may worsen bradycardia, heart block, and congestive heart failure. Other minor adverse effects of calcium channel antagonists include peripheral edema, dizziness, light-headedness, headache, nausea, and flushing, especially with nifedipine and nicardipine.

Many other agents are available to treat essential hypertension. These agents include prazosin and terazocin, $alpha_1$-adrenergic receptor antagonists whose antihypertensive effects are due to resultant arterial vasodilation; clonidine, an $alpha_2$-adrenergic agonist which acts centrally as well as peripherally at inhibitory $alpha_2$-adrenergic receptors, decreasing sympathetic response. Other centrally acting agents include methyldopa, guanabeiz, and guanfacine; reserpine, which acts by depleting stores of catecholamines; guanadrel, a peripheral adrenergic antagonist similar to guanethidine with a shorter duration of action; and direct-acting vasodilators such as hydralazine and minoxidil. These agents, although effective produce noticeable symptomatic side effects, including reflex sympathetic stimulation and fluid retention, orthostatic hypotension, and impotence.

Many antihypertensive agents activate compensatory pressor mechanisms, such as increased renin release, elevated aldosterone secretion and increased sympathetic vasoconstrictor tone, which are designed to return arterial pressure to pretreatment levels, and which can lead to salt and water retention, edema and ultimately to tolerance to the antihypertensive actions of the agent. Furthermore, due to the wide variety of side effects experienced with the present complement of antihypertensive drugs and the problems experienced therewith by special populations of hypertensive patients, including the elderly, blacks, and patients with chronic obstructive pulmonary disease, diabetes, or peripheral vascular diseases, there is a need for additional classes of drugs to treat hypertension.

Ischemia

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone. Mechanisms for vasospastic ischemia include: (i) Increased vascular tone at the site of stenosis due to increased catecholamine release: (ii) Transient intraluminal plugging and (iii) Release of vasoactive substances formed by platelets at the site of endothelial lesions.

The coronary circulation is unique since it perfuses the organ which generates the perfusion pressure for the entire circulation. Thus, interventions which alter the state of the peripheral circulation and contractility will have a profound effect on coronary circulation. The regulatory component of the coronary vasculature is the small coronary arterioles which can greatly alter their internal diameter. The alteration of the internal radius is the result of either intrinsic contraction of vascular smooth muscle (autoregulation) or extravascular compression due to ventricular contraction. The net effect of therapies on the ischemic problem involves a complex interaction of opposing factors which determine the oxygen supply and demand.

Cardioprotection and Prevention of Ischemic Injury

The development of new therapeutic agents capable of limiting the extent of myocardial injury, i.e., the extent of myocardial infarction, following acute myocardial ischemia is a major concern of modern cardiology.

The advent of thrombolytic (clot dissolving) therapy during the last decade demonstrates that early intervention during heart attack can result in significant reduction of damage to myocardial tissue. Large clinical trials have since documented that thrombolytic therapy decreases the risk of developing disturbances in the heartbeat and also maintains the ability of the heart to function as a pump. This preservation of normal heart function has been shown to reduce long-term mortality following infarction.

There has also been interest in the development of therapies capable of providing additional myocardial protection which could be administered in conjunction with thrombolytic therapy, or alone, since retrospective epidemiological studies have shown that mortality during the first few years following infarction appears to be related to original infarct size.

In preclinical studies of infarction, conducted in a variety of animal models, many types of pharmacological agents such as calcium channel blockers, prostacyclin analogs, and agents capable of inhibiting certain metabolic pathways have been shown to be capable of reducing ischemic injury in several animal species.

Recent studies have demonstrated that exposure of the myocardium to brief periods of ischemia (interruption of blood flow to the heart) followed by reperfusion (restoration of blood flow) is able to protect the heart from the subsequent ischemic injury that would otherwise result from subsequent exposure to a longer period of ischemia. This phenomenon has been termed myocardial preconditioning and is believed to be partially attributable to the release of adenosine during the preconditioning period.

Other studies have shown that adenosine and adenosine agonists reduce the extent of tissue damage that is observed following the interruption of blood flow to the heart in a variety of models of ischemic injury in several species (see, for example, Toombs. C. et al., "Myocardial protective effects of adenosine. Infarct size reduction with pretreatment and continued receptor stimulation during ischemia.", *Circulation* 86, 986–994 (1992): Thornton, J. et al., "Intravenous pretreatment with $A_1$-selective adenosine analogs protects the heart against infarction.", *Circulation* 85, 659–665 (1992); and Downey, J., "Ischemic preconditioning—nature's own cardioprotective intervention.", *Trends Cardiovasc. Med.* 2(5), 170–176 (1992)).

The processes of the present invention prepares intermediates which are useful in preparing compounds which mimic myocardial preconditioning, thereby ameliorating ischemic injury or producing a reduction in the size of myocardial infarct consequent to myocardial ischemia and are useful as cardioprotective agents.

Antilipolvsis

Hyperlipidemia and hypercholesterolemia are known to be two of the prime risk factors for atherosclerosis and coronary heart disease, the leading cause of death and disability in Western countries. Although the etiology of atherosclerosis is multifactorial, the development of atherosclerosis and conditions including coronary artery disease, peripheral vascular disease and cerbrovascular disease resulting from restricted blood flow, are associated with abnormalities in serum cholesterol and lipid levels. The etiology of hypercholesterolemia and hyperlipidemia is primarily genetic, although factors such as dietary intake of saturated fats and cholesterol may contribute.

The antilipolytic activity of adenosine and adenosine analogues arise from the activation of the $A_1$ receptor subtype (Lohse, M. J., et al., *Recent Advances in Receptor Chemistry,* Melchiorre, C. and Gianella, Eds, Elsevier Science Publishers B. V. Amsterdam, 1988, 107–121). Stimulation of this receptor subtype lowers the intracellular cyclic AMP concentration in adipocytes. Cyclic AMP is a necessary co-factor for the enzyme lipoprotein lipase which hydrolytically cleaves triglycerides to free fatty acids and glycerol in adipocytes (Egan, J. J., et al., *Proc. Natl. Acad. Sci.* 1992 (89), 8357–8541). Accordingly, reduction of intracellular cyclic AMP concentration in adipocytes reduces lipoprotein lipase activity and, therefore, the hydrolysis of triglycerides.

Elevated blood pressure and plasma lipids, including triglycerides, are two will accepted risk factors associated with mortality resulting from cardiovascular disease.

For the diabetic patient, where the likelihood of mortality from cardiovascular disease is substantially greater, the risk associated with these factors is further magnified (Bierman, E. L., *Arteriosclerosis and Thrombosis* 1992 (12), 647–656). Additionally, data suggest that excessive lipolysis is characteristic of non-insulin dependent diabetes and possibly contributes to insulin resistance and hyperglycemia (Swislocki, A. L., Horm. Metab. Res. 1993 (25), 90–95).

The processes of the present invention prepares intermediates which are useful in preparing compounds which are antihypertensive and antilipolytic agents and useful in the treatment and amelioration of both vascular and metabolic risk factors.

Adenosine Compounds And Their Activity

Adenosine has a wide variety of physiological and pharmacological action including a marked alteration of cardiovascular and renal function. In animals and man, intravenous injection of the adenosine nucleotide causes hypotension.

The physiological and pharmacological actions of adenosine are mediated through specific receptors located on cell surfaces. Two adenosine receptor subtypes designated as $A_1$ and $A_2$ receptors, have been identified. The $A_1$ receptor inhibits the formation of cAMP by suppressing the activity of adenylate cyclase, while stimulation of $A_2$ receptors increases adenylate cyclase activity and intracellular cAMP. Each receptor appears to mediate specific actions of adenosine in different tissues: for example, the vascular actions of adenosine appears to be mediated through stimulation of $A_2$ receptors, which is supported by the positive correlation between cAMP generation and vasorelaxation in adenosine-treated isolated vascular smooth muscle; while stimulation of the cardiac $A_1$ receptors reduces cAMP generation in the heart which contributes to negative dromotropic, inotropic and chroniotropic cardiac effects. Consequently, unlike most vasodilators, adenosine administration does not produce a reflex tachycardia.

Adenosine also exerts a marked influence on renal function. Intrarenal infusion of adenosine causes a transient fall in renal blood flow and an increase in renal vascular resistance. With continued infusion of adenosine, renal blood flow returns to control levels and renal vascular resistance is reduced. The initial renal vasoconstrictor responses to adenosine are not due to direct vasoconstrictor actions of the nucleotide, but involve an interaction between adenosine and the renin-angiotensin system.

Adenosine is widely regarded as the primary physiological mediator of reactive hyperemia and autoregulation of the coronary bed in response to myocardial ischemia. It has been reported that the coronary endothelium possesses adenosine $A_2$ receptors linked to adenylate cyclase, which are activated in parallel with increases in coronary flow and that cardiomyocyte receptors are predominantly of the adenosine $A_1$ subtype and associated with bradycardia. Accordingly, adenosine offers a unique mechanism of ischemic therapy.

Cardiovascular responses to adenosine are short-lived due to the rapid uptake and metabolism of the endogenous nucleotide. In contrast, the adenosine analogs are more resistant to metabolic degradation and are reported to elicit sustained alterations in arterial pressure and heart rate.

Several potent metabolically-stable analogs of adenosine have been synthesized which demonstrate varying degrees of selectivity for the two receptor subtypes. Adenosine agonists have generally shown greater selectivity for $A_1$ receptors as compared to $A_2$ receptors. Cyclopentyladenosine (CPA) and R-phenylisopropyl-adenosine (R-PIA) are standard adenosine agonists which show marked selectivity for the $A_1$ receptor ($A_2/A_1$ ratio=780 and 106, respectively). In contrast, N-5'-ethyl-carboxamido adenosine (NECA) is a potent $A_2$ receptor agonist (Ki-12 nM) but has equal affinity for the $A_1$ receptor(Ki-6.3 nM; $A_2/A_1$ ratio=1.87). Until recently, CV-1808 was the most selective $A_2$ agonist available ($A_2/A_1$=0.19), even though the compound was 10-fold less potent than NECA in its affinity for the $A_2$ receptor. In recent developments, newer compounds have been disclosed which are very potent and selective $A_2$ agonists (Ki=3–8 nM for $A_1$; $A_2/A_1$ ratio=0.027–0.042).

Various N6-aryl and N6-heteroarylalkyl substituted adenosines, and substituted-(2-amino and 2-hydroxy) adenosines, have been reported in the literature as possessing varied pharmacological activity, including cardiac and circulatory activity. See, for example, British Patent Specification 1,123,245, German Offen. 2,136,624, German Off 2,059,922, German Offen. 2,514,284, South African Patent No. 67/7630, U.S. Pat. No. 4,501,735, EP Publication No. 0139358 (disclosing N6-[geminal diaryl substituted alkyl] adenosines), EP Patent Application Ser. No. 88106818.3 (disclosing that N6-heterocyclic-substituted adenosine derivatives exhibit cardiac vasodilatory activity), German Offen. 2,131,938 (disclosing aryl and heteroaryl alkyl hydrazinyl adenosine derivatives), German Offen. 2,151,013 (disclosing N6-aryl and heteroaryl substituted adenosines), German Offen. 2,205,002 (disclosing adenosines with N6-substituents comprising bridged ring structures linking the N6-nitrogen to substituents including thienyl) and South African Patent No. 68/5477 (disclosing N6-indolyl substituted-2-hydroxy adenosines).

U.S. Pat. No. 4,954,504 and EP Publication No. 0267878 disclose generically that carbocyclic ribose analogues of adenosine, and pharmaceutically acceptable esters thereof, substituted in the 2- and/or N6-positions by aryl lower alkyl groups including thienyl, tetrahydropyranyl, tetrahydrothiopyranyl, and bicyclic benzo fused 5- or 6-membered saturated heterocyclic lower alkyl derivatives exhibit adenosine receptor agonist properties. Adenosine analogues having thienyl-type substituents are described in EP Publication No. 0277917 (disclosing N6-substituted-2-heteroarylalkylamino substituted adenosines including 2-[(2-[thien-2-yl]ethyl)amino] substituted adenosine), German Offen. 2,139,107 (disclosing N6-[benzothienylmethyl]-adenosine). PCT WO 85/04882 (disclosing that N6-heterocyclicalkyl-substituted adenosine derivatives, including N6-[2-(2-thienyl)ethyl]amino-9-(D-ribofuranosyl)-9H-purine, exhibit cardiovascular vasodilatory activity and that N6-chiral substituents exhibit enhanced activity), EP Published Application No. 0232813 (disclosing that N6-(1-substituted thienyl) cyclopropylmethyl substituted adenosines exhibit cardiovascular activity), U.S. Pat. No. 4,683,223 (disclosing that N6-benzothiopyranyl substituted adenosines exhibit antihypertensive properties), PCT WO 88/03147 and WO 88/03148 (disclosing that N6-[2-aryl-2-(thien-2-yl)]ethyl substituted adenosines exhibit antihypertensive properties), U.S. Pat. Nos. 4,636,493 and 4,600,707 (disclosing that N6-benzothienylethyl substituted adenosines exhibit antihypertensive properties).

Adenosine-5'-carboxylic acid amides are disclosed as having utility as anti-hypertensive and anti-anginal agents in U.S. Pat. No. 3,914,415, while U.S. Pat. No. 4,738,954 discloses that N6-substituted aryl and arylalkyl-adenosine 5'-ethyl carboxamides exhibit various cardiac and antihypertensive properties.

$N^6$-alkyl-2'-O-alkyl adenosines are disclosed in EP Publication No. 0,378,518 and UK Patent Application 2,226,027 as having antihypertensive activity. $N^6$-alkyl-2',3'-di-O-alkyl adenosines are also reported to have utility as antihypertensive agents, U.S. Pat. No. 4,843,066.

Adenosine-5'-(N-substituted)carboxamides and carboxylate esters and N1-oxides thereof are reported to be coronary vasodilators, Stein. et al., *J. Med. Chem,*. 1980, 23, 313–319 and *J. Med. Chem.* 19 (10), 1180 (1976). Adenosine-5'-carboxamides and N1-oxides thereof are also reported as small animal poisons in U.S. Pat. No. 4,167,565.

The antilipolytic activity of adenosine is described by Dole. V. P., *J. Biol. Chem.* 236 (12), 3125–3130(1961). Inhibition of lipolysis by (R)-$N^6$ phenylisopropyl adenosine is disclosed by Westermann, E., et al., *Adipose Tissue, Regulation and Metabolic Functions,* Jeanrenaud, B. and Hepp, D. Eds., George Thieme, Stuttgart, 47–54 (1970). $N^6$-mono- and disubstituted adenosine analogues are disclosed as having antilipolytic, antihypercholesterolemic, and antihyperlipemic activity in U.S. Pat. Nos. 3,787,391, 3,817, 981, 3,838,147, 3,840,521, 3,835,035, 3,851,056, 3,880,829, 3,929,763, 3,929,764, 3,988,317, and 5,032,583.

It is believed that the reported toxicity, CNS properties and heart rate elevation associated with adenosine analogues have contributed to the difficulties preventing the development of a commercial adenosine analog antihypertensive/antiischemic agent.

U.S. patent application Ser. Nos. 08/484,811 and 08/316/761, which claim benefit of published PCT Application PCT/US91/06990, disclose a class of metabolically stable adenosine agonists, and derivatives thereof, possessing unexpectedly desirable pharmacological properties. i.e., anti-hypertensive, cardioprotective, anti-ischemic, and anti-lipolytic agents having a unique therapeutic profile.

2. Reported Developments

SUMMARY OF THE INVENTION

The present invention is directed to a process for preparing 2,4-dihydroypyridine comprising heating a compound of the formula A

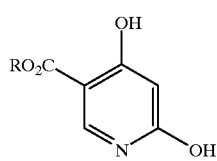

(A)

wherein R is H, alkyl or aralkyl and phosphoric acid where the ratio of phosphoric acid to water is not less than about 27 to 1 weight %. The invention is also directed to a process for preparing 2,4-dihydroy-3-nitropyridine comprising reacting 2,4-dihydroypyridine with nitric acid.

The processes of the present invention prepare intermediates which are useful in preparing compounds which are useful for treating cardiovascular disease marked by hypertension or myocardial ischemia, ameliorating ischemic injury or myocardial infarct size, or treating hyperlipidemia or hypercholesterolemia.

DETAILED DESCRIPTION

As used above and throughout the description of the invention, the following terms, unless otherwise indicated, shall be understood to have the following meanings:

"Acyl" means a straight or branched alkyl-C(=O)-group. Preferred acyl groups are lower alkanoyl having from 1 to about 6 carbon atoms in the alkyl group.

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain.

"Lower alkyl" means an alkyl group having 1 to about 6 carbons.

"Alkylene" means a straight or branched bivalent hydrocarbon chain having from 1 to about 20 carbon atoms. The preferred alkylene groups are the lower alkylene groups having from 1 to about 6 carbon atoms. The most preferred alkylene groups are methylene, ethylene, ethylethylene, methylethylene and dimethylethylene.

"Cycloalkylene" means a 1,2- or 1,3-bivalent carbocyclic group having about 4 to about 8 carbon atoms. Preferred cycloalkylene groups include 4,5-cis- or trans-cyclohexylene, 1,2-cyclohexylene and 1,2-cyclopentylene.

"Cycloalkenylene" means a 1,2- or 1,3-bivalent carbocyclic group having about 4 to about 8 carbon atoms and a double bond. A representative cycloalkenylene group is 4,5-cis- or trans-cyclohexenylene.

"Optionally substituted" means that a given substituent or substituents both may or may not be present.

"Alkyl amino" means an amino group substituted by one or two alkyl groups. Preferred groups are the lower alkyl amino groups.

"Alkyl carbamoyl" means a carbamoyl group substituted by one or two alkyl groups. Preferred are the lower alkyl carbamoyl groups.

"Alkyl mercaptyl" means an alkyl group substituted by a mercaptyl group. Mercaptyl lower alkyl groups are preferred.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group, as previously described, substituted by an alkoxy group, as previously described.

"Aralkyl" means an alkyl group substituted by an aryl radical, wherein "aryl" means a phenyl or phenyl substituted with one or more substituents which may be alkyl, alkoxy, amino, nitro, carboxy, carbalkoxy, cyano, alkyl amino, halo, hydroxy, hydroxyalkyl, mercaptyl, alkylmercaptyl, acyl or carbamoyl.

"Carbalkoxy" means a carboxyl substituent esterified with an alcohol of the formula $C_nH_{2n+1}OH$, wherein n is from 1 to about 6.

"Halogen" (or "halo") means chlorine (chloro), fluorine (fluoro), bromine (bromo) or iodine (iodo).

"Heterocyclyl" means about a 4 to about a 10 membered ring structure in which one or more of the atoms in the ring is an element other than carbon, e.g., N, O or S.

"Formula I" is described by the following formula and definitions:

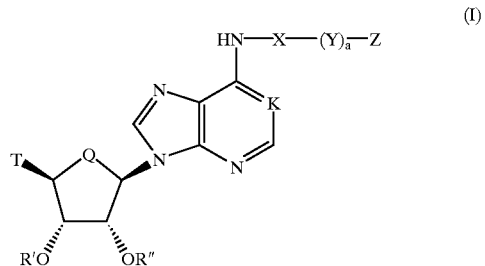

(I)

wherein:

K is N, N →O, or CH;

Q is $CH_2$ or O;

T is

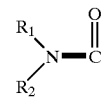

X is a straight or branched chain alkylene, cycloalkylene or cycloalkenylene group, each of which is optionally substituted by at lease one $CH_3$, $CH_3CH_2$, Cl, F, $CF_3$, or $CH_3O$;

Y is $NR_4$, O or S;

a=0 or 1;

Z is of the formula $Z_1$ is N, $CR_5$, $(CH)_m$—$CR_5$ or $(CH)_m$—N, m being 1 or 2;

$Z_2$ is N, $NR_6$, O or S, n being 0 or 1;

$R_1$, $R_2$, $R_3$, $R_4$, $R_5$ and $R_6$ are independently H, alkyl, aryl or heterocyclyl;

$R_a$ and $R_b$ are independently H, OH, alkyl, hydroxyalkyl, alkyl mercaptyl, thioalkyl, alkoxy, alkyloxyalkyl, amino, alkyl amino, carboxyl, acyl, halogen, carbamoyl, alkyl carbamoyl, aryl or heterocyclyl; and R' and R" are independently hydrogen, alkyl, aralkyl, carbamoyl, alkyl carbamoyl, dialkylcarbamoyl, acyl, alkoxycarbonyl, aralkoxycarbonyl, aryloxycarbonyl, or R' and R" together may form wherein $R_c$ is hydrogen or alkyl, where $R_d$ and $R_e$ are independently hydrogen, alkyl, or together with the carbon atom to which they are attached may form a 1,1-cycloalkyl group;

provided that when X is straight chain alkylene and Q is oxygen, then Z represents a heterocyclyl including at least two heteroatoms;

or a pharmaceutically acceptable salt thereof.

Representative heterocyclic moieties comprising the N6 substituent of the compounds of Formula I include the following:

Preferred heterocyclic groups include unsubstituted and substituted thienyl, thiazolyl and benzothiazolyl groups, wherein the substituents may be one or more members of the group of alkoxy, alkylamino, aryl, carbalkoxy, carbamoyl, cyano, halo, hydroxy, mercaptyl, alkylmercaptyl or nitro.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl and 3-hydroxypropyl.

"Pro-drug" means a compound which may or may not itself be biologically active but which may, by metabolic, solvolytic, or other physiological means be converted to a biologically active chemical entity.

"Cardioprotection" refers to the effect whereby the myocardium is made less susceptible to ischemic injury and myocardial infarct consequent to myocardial ischemia.

"Amelioration of ischemic injury" means the prevention or reduction of ischemic injury to the myocardium consequent to myocardial ischemia.

"Amelioration of myocardial infarct size" means the reduction of the myocardial infarct size, or the prevention of myocardial infarct, consequent to myocardial ischemia.

The compounds of Formula I include preferably a chiral (asymmetric) center. For example, preferred compounds having such asymmetric center comprise compounds e.g. wherein X is isopropylene, and have either an R or S configuration, the R configuration being most preferred. The compounds of Formula I include the individual stereoisomers and mixtures thereof. The individual isomers are prepared or isolated by methods well known in the art or by methods described herein.

The compounds herein prepared from the intermediates prepared according to the invention may be used in the form of the free base, in the form of acid addition salts or as hydrates. All such forms are within the scope of the compounds of Formula I. Acid addition salts are simply a more convenient form for use. In practice, use of the salt form inherently amounts to use of the base form. The acids which may be used to prepare the acid addition salts include preferably those which produce, when combined with the free base, pharmaceutically acceptable salts, that is, salts whose anions are non-toxic to the recipient in pharmaceutical doses of the salts, so that the beneficial antihypertensive, cardioprotective, anti-ischemic, and antilipolytic effects produced by the free base are not vitiated by side effects ascribable to the anions. Although pharmaceutically acceptable salts of the compounds herein are preferred, all acid addition salts are useful as sources of the free base form, even if the particular salt, per se, is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid, and sulfamic acid: and organic acids such as acetic acid, citric acid, lactic acid, tartaric acid, malonic acid, methanesulfonic acid, fumaric acid, ethanesulfonic acid, benzenesulfonic acid, p-toluenesulfonic acid, cyclohexylsulfaunic acid, quinic acid and the like. The corresponding acid addition salts comprise the following: hydrochloride, sulfate, phosphate, sulfamate, acetate, citrate, lactate, tartarate. methanesulfonate, fumarate, ethanesulfonate, benzenesulfonate, p-toluenesulfonate, cyclohexylsulfonate and quinate, respectively.

The acid addition salts of the compounds of the compounds of Formula I are conveniently prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Included within the scope of Formula I are classes of compounds which may be characterized generally as N6-heterocyclic-substituted adenosines: N6-heterocyclic-substituted carbocyclic adenosines (or, alternatively, dihydroxy[N6-heterocyclic substituted-9-adenyl] cyclopentanes) and N-oxides thereof: and N6-heterocyclic-substituted-N'-1-deazaaristeromycins (or, alternatively, dihydroxy[N7-heterocyclic-substituted[4,5-b] imidazopyridyl]-cyclopentanes). Also within the scope of Formula I are the 5'-alkylcarboxamide derivatives of the adenosines, the carbocyclic adenosines and the 1-deazaaristeromycins, the derivatives of compounds of the above classes in which one or both of the 2- or 3-hydroxyl groups of the cyclopentane ring or, in the cases of classes of compounds containing the ribose moiety, the 2'- or 3'-hydroxyl groups of the ribose ring are substituted. Such derivatives may themselves comprise the biologically active chemical entity useful in the treatment of hypertension and myocardial ischemia, and as cardioprotective and antilipolytic agents, or may act as pro-drugs to such biologically active compounds which are formed therefrom under physiological conditions.

Representative compounds of the invention include: N6-[trans-2-(thiophen-2-yl)cyclohex-4-en-1-yl]adenosine; N6-[trans-2-(thiophen-3-yl)-cyclohex-4-en-1-yl]adenosine; N6-[trans-2-(thiophen-2-yl)cyclohex-4-en-1-yl]adenosine-5'-N-ethyl carboxamide; N6-[2-(2'-aminobenzothiazolyl)ethyl] adenosine; N6-[2-(2'-thiobenzothiazolyl)ethyl]adenosine; N6-[2-(6'-ethoxy-2'-thiobenzothiazolyl)ethyl]adenosine; N6-[2-(2'-aminobenzothiazolyl)ethyl]adenosine-5'-N-ethyl carboxamide; N6-[2-(2'-aminothiazolyl)ethyl]carbocyclic adenosine-5'-N-ethyl carboxamide; N6-[2-(4'-methylthiazol-5'-yl)ethyl]adenosine; N6-[2-(2'-thiazolyl) ethyl]adenosine; N6-[(R)-1-(5'-chlorothien-2'-yl)-2-propyl] adenosine-5'-N-ethyl carboxamide; N6-[2-(2'-methyl-4'-thiazolyl)-ethyl]adenosine; N6-[(R)-1-methyl-2-(2'-benzo[b]thiophenyl)ethyl]adenosine; N6-[2-(4"-methyl-5"-thiazolyl)ethyl]carbocyclic adenosine-5'-N-ethyl carboxamide; N6-[2-(2"-thiazolyl)ethyl]carbocyclic adenosine-5'-N-ethyl carboxamide; N6-[2-(4'-phenyl-2'-thiazolyl)ethyl]adenosine; N6-[(R)-1-(5"-chloro-2"-thienyl) prop-2-yl]carbocyclic adenosine-5'-N-ethyl carboxamide; (−)-N6-[thiophen-2"-yl)ethan-2-yl]carbocyclic adenosine-5'-N-ethyl carboxamide; N6-[1-(thiophen-3-yl)ethan-2-yl] carbocyclic adenosine-5'-N-ethyl carboxamide; N6-[(R)-1-((thiophen-2-yl)prop-2-yl)]carbocyclic adenosine-5'-N-ethyl carboxamide; N6-[1-(thiophen-2-yl)ethan-2-yl]-N'-1-deazaaristeromycin-5'-N-ethyl carboxamide; N6-[(R)-1-((thiazo-2-yl)-prop-2-yl)]adenosine-5'-N-ethyl carboxamide; N6-[1-(thiophen-2-yl)-2-methylpropyl] adenosine-5'-N-ethyl carboxamide; N6-[(R)-1-(5'-chlorothien-2-yl)-2-butyl]carbocyclic adenosine-5'-N-ethylcarboxamide; N6-[2-(4'-methyl-2'-thiazolyl)ethyl] adenosine; N6-[4'-phenyl-2'-thiazolyl)methyl]adenosine; (−)-[2S-[2a,3a-dimethylmethylenedioxy-4-β-[N6-[2-(5-chloro-2-thienyl)-(1R)-1-methylethyl]amino]-9-adenyl] cyclopentane]-1-β-N-ethylcarboxamide; (2S)-2a,3a-dihydroxy-4β-[N6-[2-(5-chloro-2-thienyl)-(1R)-1-methylethyl]amino-9-adenyl]cyclopentane-1β-N-ethylcarboxamide: (2S)-2a,3a-dihydroxy-4-[N6-[2-(5-chloro-2-thienyl)-(1R)-1-methylethyl]amino-9-adenyl] cyclopentane-1β-N-ethylcarboxamide-N$^1$-oxide; [1S-[1a,2b,3b,4a(S*)]]-4-[7-[[2-(5-chloro-2-thienyl)-1-methylethyl]amino]-3H-imidazo[4,5-b]pyridin-3-yl]-N-ethyl-2,3-dihydroxycyclopentane-carboxamide; [1S-[1a,2b,3b,4a]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide; [1S-[1a,2b,3b,4a]]-4-[7-[[2-(2-thienyl)-1-isopropylethyl]amino]-3H-imidazo[4,5-b]pyridin-3-yl]-N-ethyl-2,3-dihydroxycyclopentanecarboxamide; [1S-[1a,2b,3b,4a(S*)]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide; [1S-[1a,2b,3b,4a(S*)]]-4-[7-[[2-(2-thienyl)-1-methylethyl]amino]-3H-imidazo[4,5-b]pyridin-3-yl]-N-ethyl-2,3-dihydroxycyclopentane-carboxamide; [1S-[1a,2b,3b,4a]]-4-[7-[[2-(5-chloro-2-thienyl)-1-ethylethyl]amino]-3H-imidazo[4,5-b]pyridin-3-yl]-N-ethyl-2,3-dihydroycyclopentate-carboxamide; (2S)-2a,3a-bis-methoxycarbonyloxy-4-[N6-[2-(5-chloro-2-thienyl)-(1R)-1-methylethyl]amino-9-adenyl]cyclopentane-1β-N-ethylcarboxamide; (2S)-2a,3a-dihydroxy-4β-[N6-[2-(5-chloro-2-thienyl)-(1R)-1-methylethyl]amino-9-adenyl] cyclopentane-1β-N-ethylcarboxamide ethoxymethylene acetal; (2S)-2a,3a-dihydroxy-4β-[N6-[2-(5-chloro-2-thienyl)-(1R)-1-methylethyl]amino-9-adenyl]cyclopentane-1β-N-ethylcarboxamide-2,3-carbonate; (2S)-2a3a-bis-methylcarbamoyloxy-4β-[N6-[2-(5-chloro-2-thienyl)-(1R)-1-methylethyl]amino-9-adenyl]cyclopentane-1βN-ethylcarboxamide; (2S)-2a,3a-dihydroxy-4β-[N6-[2-(5-chloro-2-thienyl)-(1R)-1-methylethyl]amino-9-adenyl] cyclopentane-1β-N-ethylcarboxamide-2,3-thiocarbonate; N$^6$-[2-(3-chloro-2-thienyl)-(1R)-1-methylethyl]-2'-O-methyladenosilne: N$^6$-[2-(5-chloro-2-thienyl)-(1R)-1-methylethyl]-2'-O-methyladenosine; and N$^6$-[trans-5-(2-thienyl)cyclohex-1-en-4-yl]-2'-O-methyladenosine.

A preferred class of compounds described by Formula I wherein R' and R" are H.

Another preferred class of compounds of Formula I are the 5'-N-alkylcarboxamide derivatives of the N6-heterocyclic-substituted carbocyclic adenosines, in other words, the compounds of Formula I, wherein K is N, Q is $CH_2$ and T is $R_1R_2N-C=O$, or pharmaceutically acceptable salts thereof.

Still another preferred class of compounds of Formula I are the 5'-N-alkylcarboxamide derivatives of the N6-heterocyclic-substituted-N'-1-deazaaristeromycins. i.e., the 4-[7-[heterocyclylamino]-3H-imidazo[4,5-b]pyridin-3-yl]-alkyl-2,3-dihydroxycyclopentanecarboxamides, in other words, the compounds of Formula I, wherein K is CH, Q is $CH_2$, and T is $R_1R_2N-C=O$, or pharmaceutically acceptable salts thereof.

The most preferred class of compounds of Formula I are characterized by the presence of a chiral center alpha to the N6 atom of the purine or 1-deazapurine ring, while a special embodiment of this class includes compounds characterized by a chiral ethyl group attached to the carbon atom alpha to the N6-nitrogen. A particularly preferred class of compounds are characterized by an N6-[1-loweralkyl-2-(3-halothien-2-yl)ethyl]substituent group.

Most preferred embodiments of the compounds of Formula I comprise the compounds (−)-[2S-[2a,3a-dihydroxy-4β-[N6-[2-(5-chloro-2-thienyl)-1-(R)-methylethyl]-amino]-9-adenyl]cyclopentane-1β-ethylcarboxamide, (−)-[2S-[2a,3a-dihydroxy-4β-[N6-[1-(R)-ethyl-2-(3-chloro-2-thienyl) ethyl]amino]-9-adenyl]cyclopentane-1β-ethylcarboxamide, [1S-[1a,2b,3b,4a(S*)]]-4-[7-[[2-(5-chloro-2-thienyl)-1-methylethyl]amino]-3H-imidazo[4,5-b]pyridin-3-yl]-N-ethyl-2,3-dihydroxycyclopentanecarboxamide, [1S-[1a,2b,3b,4a(S*)]]-4-[7-[[2-(3-chloro-2-thienyl)-1-ethylethyl] amino]-3H-imidazo[4,5-b]pyridin-3-yl]-N-ethyl-2,3-dihydroxycyclopentanecarboxamide, and pharmaceutically acceptable salts thereof.

The compounds of Formula I may be prepared by known methods or in accordance with the reaction sequences described below. The starting materials used in the preparation of compounds of Formula I are known or commercially available, or can be prepared by known methods or by specific reaction schemes described herein which include the processes according to the invention.

The processes according to the invention for preparing 2,4-dihydroxypyridine and 2,4-dihydroxy-3-nitropyridine are shown in Scheme A1.

tinic acid. According to this aspect of the invention, the reaction involves a decarboxylation from a pyridyl moiety catalyzed by phosphoric acid under substantially dehydrated conditions.

According to another aspect of the invention, alternatively in Scheme A1 2,4-dihydroxypyridine may be prepared by converting the (alkyl or aralkyl) 4,6-dihydroxy nicotinate to 4,6-dihydroxy nicotinic acid by hydrolyzing with a strong

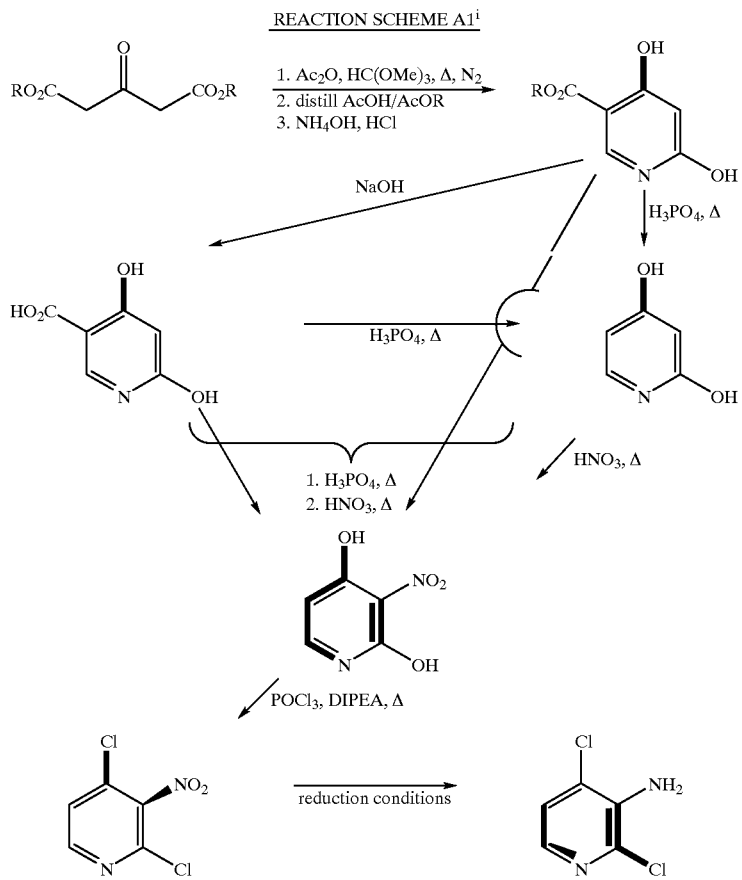

Scheme A1 shows the initial formation of an (alkyl or aralkyl) 4,6-dihydroxy nicotinate by reacting a di(alkyl or aralkyl) acetone dicarboxylate with trimethylorthoformate and acetic anhydride under an inert atmosphere such as nitrogen, distilling acetic acid/(alkyl or aralkyl) acetate (preferably under reduced pressure such as about 20 mm Hg), and reacting sequentially the resultant mixture with ammonium hydroxide and hydrochloric acid.

According to one aspect of the invention, following the formation of the (alkyl or aralkyl) 4,6-dihydroxy nicotinate in Scheme A1, that product is converted to 2,4-dihydroxypyridine by heating with phosphoric acid where the ratio of phosphoric acid to water is not less than about 27 to 1 weight % ($H_3PO_4$: $H_2O$=~27:1 wt %). The ratio may be obtained heating to a temperature whereupon a sufficient amount of water is removed from the reaction mixture. Upon the removal of that sufficient amount of water the temperature of the reaction mixture reaches a temperature of about 210° C. (±5° C.). This reaction mixture is then maintained for about 4 to about 5 hours at that approximate temperature until the disappearance of the (alkyl or aralkyl) 4,6-dihydroxy nicotinate or intermediate 4,6-dihydroxy nicobase such as NaOH or KOH, and then treating the 4,6-dihydroxy nicotinic acid in the same manner as the (alkyl or aralkyl) 4,6-dihydroxy nicotinate.

According to further aspect of the invention, Scheme A1 also shows that the (alkyl or aralkyl) 4,6-dihydroxy nicotinate or 4,6-dihydroxy nicotinic acid may be converted to 2,4-dihydroxy-3-nitropyridine without isolating 2,4-dihydroxypyridine. This reaction involves carrying out the decarboxylation as described above, and then treating the reaction mixture with nitric acid. The addition of an organic acid solvent such as acetic acid s preferred before treating with the nitric acid. The nitration takes place preferably under heated conditions such as at a temperature from about 80° C. to about 100° C., more preferably at 90° C., until water is added and the heating stopped.

According to yet another aspect of the invention, Scheme A1 shows that 2,4-dihydroxypyridine may be converted to 2,4dihydroxy-3-nitropyridine applying the prior nitration method.

Scheme A1 also shows the conversion of 2,4dihydroxy-3-nitropyridine to 2,4-dichloro-3-nitropyridine by reacting phosphorus oxychloride and 2,4-dihydroxy-3-nitropyridine in the presence of diisopropylethylaminie (DIPEA). This reaction takes place at about 100° C. The 2,4-dichloro-3-nitropyridine may be used in place of other dihalonitroheteroaryls to form intermediates as shown herein, such as Scheme K.

Lastly, Scheme A1 shows the conversion of 2,4-dichloro-3-nitropyridine to 3-amino-2,4-dichloropyridine under reducing conditions such as Zn/HCl or hydrogenation conditions. The 3-amino-2,4-dichloropyridine may be used in place of other aminodihaloheteroaryls as shown herein, such as Scheme B.

Compounds of Formula I, wherein K is N, Q is O and T is $R_3O$—$CH_2$, may be prepared by reacting commercially-available 6-chloropurine riboside with various heterocyclic amines as exemplified below.

Compounds of Formula I, wherein K is N, Q is O and T is $R_1R_2N$—C=O are similarly prepared starting with the product of Reaction Scheme A. In this reaction, 6-chloropurine riboside, with the 2'- and 3'-hydroxyl groups of the ribose ring protected is treated with an oxidant, for example a Jones reagent, and the product acid treated with either dicyclohexlcarbodiimide (DCC) or BOP-Cl in the presence of a selected amine, to yield the 5'-alkylcarboxamide derivative.

REACTION SCHEME A

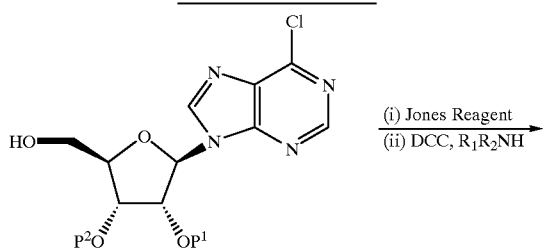

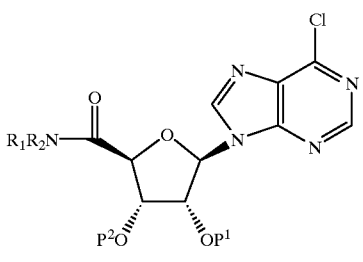

(P = protecting group)

Suitable starting materials for compounds of Formula I wherein K is N, Q is $CH_2$ and T is $R_1R_2N$—C=O, may be prepared as described by Chen et al., Tetrahedron Letters 30: 5543–46 (1989). Alternatively, Reaction Scheme B may be used to prepare such starting materials. In carrying out Reaction Scheme B, the 4-ethylcarboxamide derivative of 2,3-dihydroxycyclopentylamine, prepared as described by Chen et al., is reacted with 3-amino-2,4-dichloropyrimidine. The product of this initial reaction is then heated with an aldehydylamidine acetate, for example formamidine acetate in dioxane and methoxyethanol, for a time sufficient to effect ring closure (from about 30 min to about 4 hours), thereby yielding a product which may be conveniently reacted with various heterocyclic amines in the manner described below, to give the compounds of the invention. The order of reaction is not critical. For example, the intermediate formed in Reaction Scheme B could be reacted with a heterocyclic amine, followed by ring closure to yield the desired final product.

REACTION SCHEME B

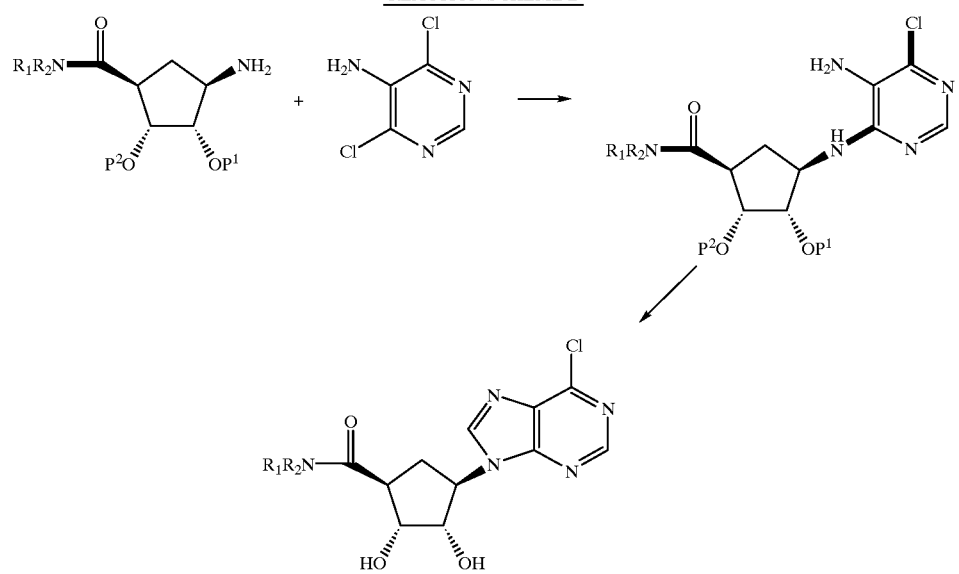

Various heterocyclic amines, useful in forming the compounds of this invention, may be prepared by one or more of the reactions shown in Reaction Schemes C–J and preparative Examples B through F, and 50 through 74, hereinbelow (Het=heterocyclic group; Halo=halogen; R=e.g. H or lower alkyl; $R_a$ and Y are as previously described).
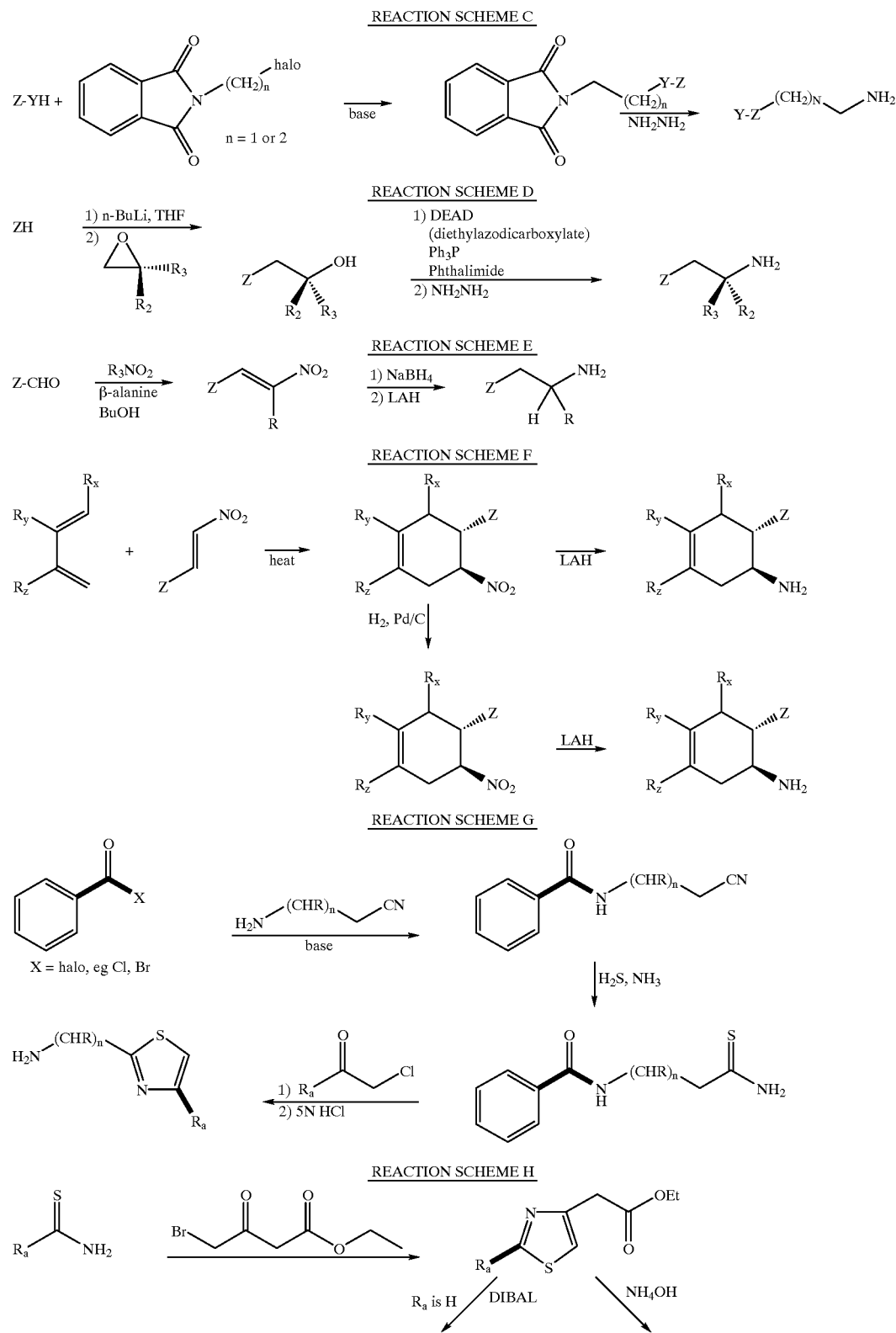

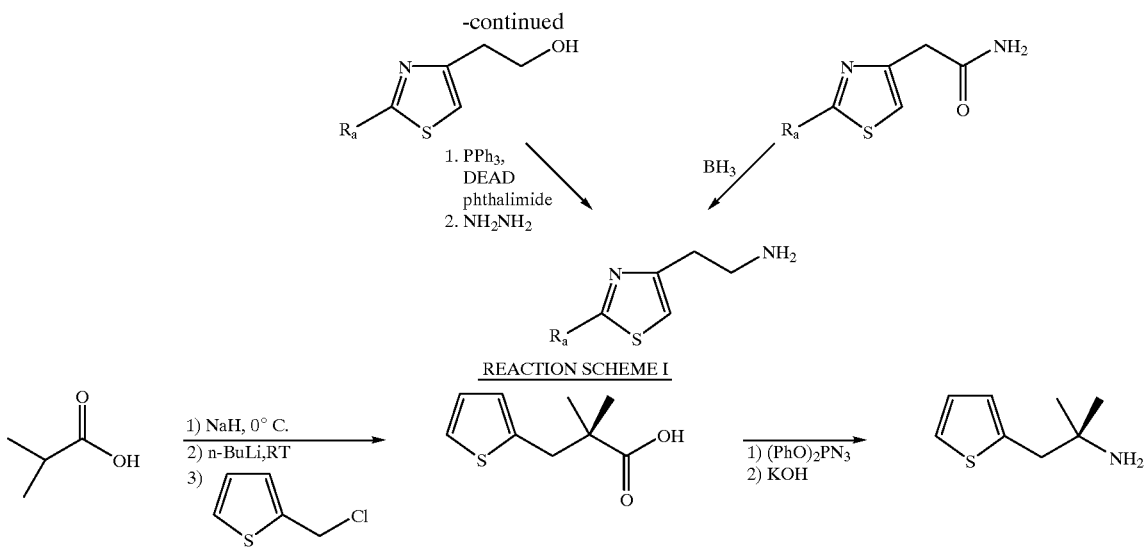

REACTION SCHEME I

The reaction sequence of Scheme I above is described in U.S. Pat. No. 4,321,398, with pertinent information incorporated herein by reference.

EXAMPLE B

Preparation of 1-(thiophen-3-yl)ethylamine

3-Thiophencarboxaldehyde (1 mmole), nitromethane (1.5 mmole) and beta-alanine (0.1 mmole) in butanol for 6 hours to give 3-nitrovinylene-thiophene, which is reduced with lithium aluminum hydride (2.5 mmole) to yield the desired product amine.

3-Substituted thienylalkylamines are prepared by substituting 3-substituted thiophenes, such as 3-chlorothiophene, for the thiophene starting materials in Example B above.

EXAMPLE C

Preparation of trans-2-(thiophen-2-yl)cyclohex-4-enylamine

A mixture of 1,3-butadiene (5 mL) and 2-nitrovinyleniethiophene (7 g) in toluene is heated at 140° C. overnight in a sealed tube. The resulting nitro-cyclohexene is hydrogenated (~35 psi $H_2$) (5% Pd/C MeOH) and treated with lithium aluminum hydride (2.5 g). The racemic trans-2-(thiophen-2-yl)-cyclohexylamine is obtained with a standard workup.

EXAMPLE D

General Preparation of 2-substituted Thiazole Amines

Benzoyl chloride and aminoethylcyanide are reacted to give N-benzoyl-aminoethylcyanide, which is reacted with hydrogen sulfide in ammonia to yield the thioamide, which is reacted with an appropriate a-halo ketone to yield the desired thiazole. Treatment with 5N hydrochloric acid removes the protecting benzoyl group to give the desired amine product.

EXAMPLE E

General Preparation of 4-Substituted Thiazolyl Amines

A preferred synthesis for 2-(2'-methyl-4'-thiazolyl) ethylamine is by reacting thioacetamide with ethyl monobromoacetoacetate to give a thiazole ester which is reduced preferably with sodium borohydride to yield the alcohol which is converted to the amine. A preferred means to the amine comprises treatment with (i) diethylazodicarboxylate, triphenylphosphine and phthalimide and (2) hydrazine hydrate.

The preparation of 4-substituted thiazole amines may also be carried out by using the foregoing reaction scheme by reacting a substituted thioamide and ethylmonobromoacetoacetate. Conversion of the resulting thiazolyl ester to the amide is effected with aqueous ammonia and the amine is formed by reduction with borane. An exemplary preparation of 2-(1,1-dimethyl-1'-thiophenyl)ethylamine is described in U.S. Pat. No. 4,321,398.

Diastereomeric mixtures of compounds or intermediates obtained in Reaction Schemes A–I above may be separated into single racemic or optically active enantiomers by methods known in the art; for example, by chromatography, fractional distillation or fractional crystallization of d- or 1-(tartarate, dibenzoyltartarate, mandelate or camphorsulfonate) salts.

EXAMPLE F

Preparation of (+) and (−) trans-2-(thiophen-2-yl) cyclohex-4-enylamine (S)-(+)Mandelic acid (0.55 eq) is added to an isopropanol solution of the racemic amine (3.4 g) prepared in Example C. The precipitate is recrystallized from isopropanol to provide 1.78 g of the salt ($[a]_D RT=+4.13$ (c=1.3, MeOH)). The amines are isolated by extracting the neutralized salts (sat. $NaHCO_3$) with $CH_2Cl_2$, drying ($Na_2SO_4$) and concentrating to provide the free amines partially resolved.

Approximately 1 g of the levorotatory amine ($[a]_D RT=−25.8$ (c=1.54, MeOH)) is treated with 2 g of 1-(−)-dibenzoyl tartaric acid in methanol and the resulting salt is worked up to provide 0.64 g of the levorotatory amine ($[a]_D RT=−28.8$ (c=1.65. MeOH)). High-field NMR analysis of the MPTA amide of the levorotatory amine revealed >96% enantiomeric excess.

Approximately 1.6 g of the enriched dextrorotatory amine mixture is treated with 3.2 g of d(+)-dibenzoyl tartaric acid in methanol. After worktip, 0.87 g of the dextrorotatory amine is obtained ($[a]_D RT=+25.8$ (c=1.67, MeOH)).

The N6-heterocyclic-substituted adenosines and carbocyclic adenosines of the invention may be formed by reacting 6-chloropurine riboside or the products of Reactions Scheme A or B with various heterocyclic amines, according to the synthetic route shown below in Reaction Scheme J, wherein K, P, Q and T are as previously defined.

REACTION SCHEME J

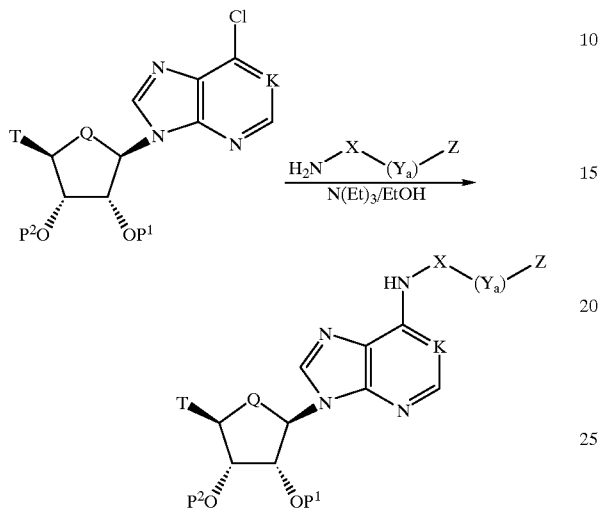

The N6-heterocyclic-substituted-N'alkyl-deazaansteromycins of the invention may be prepared as shown in Reaction Scheme K.

REACTION SCHEME K

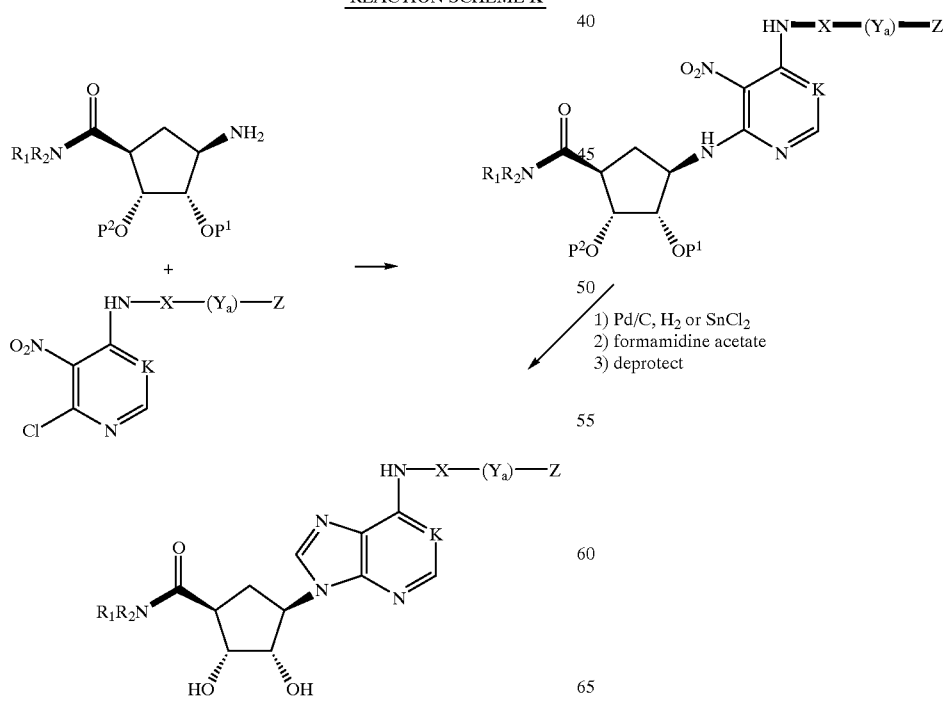

Compounds of Formula I which may act as pro-drugs include those compounds wherein the hydroxyl groups on the ribose or cyclopentane ring are substituted with groups R' and R" as defined above for Formula I. These may be prepared by known methods and are exemplified by the preparations shown in Reaction Scheme L, below.

triethylamine, will give the corresponding bis-carbonate. The alkoxymethylene acetal may be prepared by treatment with the corresponding orthoester in the presence of a catalytic amount of p-toluenesulfonic acid. The carbonate is available by treatment with 1,1'-carbonyldiimidazole and the thiocarbonate by treatment with thiocarbonyldiimidi-

REACTION SCHEME L

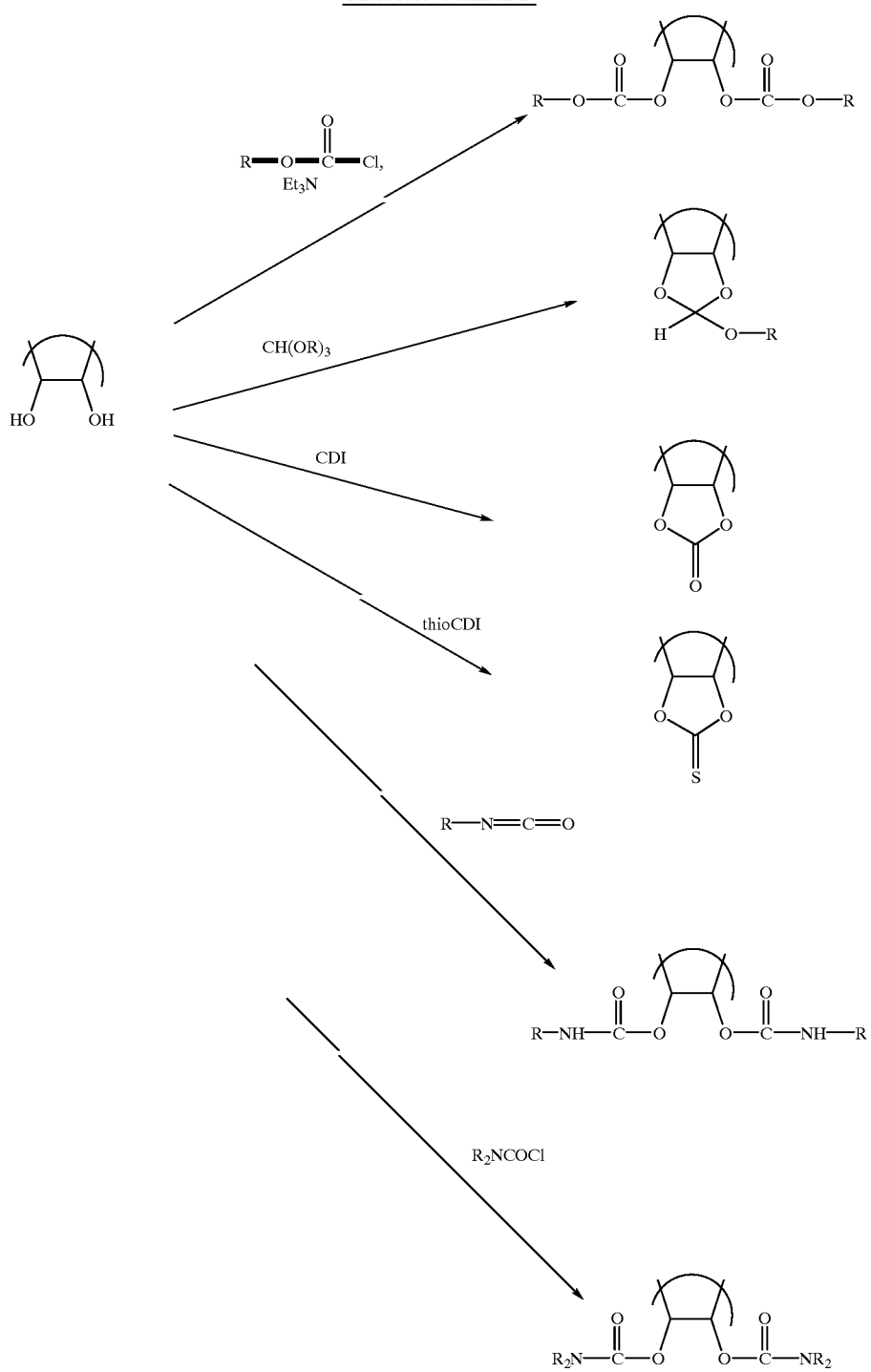

Treatment of the dihydroxy compounds with a chloroformate ester in the presence of an organic base, for example zole. The alkyl and dialkylcarbamoyl derivatives may be prepared by treatment with the corresponding alkyl isocyanate or dialkyl carbamoyl chloride in the presence of an organic base respectively.

Compounds of Formula I wherein K is N→O, i.e., the N-oxides, may be prepared by oxidation of the corresponding adenosine or carbocyclic adenosine by known methods, for example by treatment with hydrogen peroxide in acetic acid.

The 2'-O-alkyl derivatives may be prepared by known methods, for example by reaction of the appropriate heterocyclyl amine with 6-chloro-9-(2'-O-methyl-b-D-ribofuranosyl)-9H-purine.

Functional groups of starting compounds and intermediates that are used to prepare the compounds of Formula I may be protected by common protecting groups known in the art. Conventional protecting groups for amino and hydroxyl functional groups are described, for example, in T. W. Greene, "Protective Groups in Organic Synthesis", Wiley. New York (1984).

Hydroxyl groups may be protected as esters, such as acyl derivatives, or in the form of ethers. Hydroxyl groups on adjacent carbon atoms may advantageously be protected in the form of ketals or acetals. In practice, the adjacent 2' and 3' hydroxyl groups of the starting compounds in Reaction Schemes A and B are conveniently protected by forming the 2',3' isopropylidene derivatives. The free hydroxyls may be restored by acid hydrolysis, for example, or other solvolysis or hydrogenolysis reactions commonly used in organic chemistry.

Following synthesis, compounds of Formula I are typically purified by medium pressure liquid chromatography (MPLC), on a chromatotron, radially accelerated thin layer chromatography, flash chromatography or column chromatography through a silica gel or Florsil matrix, followed by crystallization. For compounds of Formula I wherein K is N, Q is O and T is $R_3O$—$CH_2$, typical solvent systems include chloroform:methanol, ethyl acetate:hexane, and methylene chloride:methanol. Eluates may be crystallized from methanol, ethanol, ethyl acetate, hexane or chloroform.

For compounds of Formula I, wherein K is N, Q is On and T is $R_1R_2N$—C=O, typical solvent systems include chloroform:methanol. Eluates may be crystallized from 50–100% ethanol (aqueous).

For compounds of Formula I, wherein Q is $CH_2$, K is N or CH, and T is $R_1R_2N$—C=O, typical solvent systems include methylene chloride:methanol. Eluates may be crystallized from ethyl acetate with or without methanol, ethanol or hexane.

Compounds requiring neutralization may be neutralized with a mild base such as sodium bicarbonate, followed by washing with methylene chloride and brine. Products which are purified as oils are sometimes triturated with hexanel-ethanol prior to final crystallization.

An improved method for preparing a substantially optically pure 2-substituted-2-amino-1-(heteroar-2- or 3-yl) ethane derivative is also described herein. 2-(Heteroaryl) ethylamines and alkyl and phenyl derivatives thereof have been prepared by a variety of means including reduction of 2-b-nitrovinylheteroaryl compounds prepared from the heteroarylformaldehydes (see, e.g., W. Foye and S. Tovivich, J. Pharm. Scien. 68 (5), 591 (1979). S. Conde. et al., J. Med. Chem. 21(9), 978 (1978), M. Dressier and M. Joullie, J. Het. Chem. 7. 1257 (1970)); reduction of cyanomethylheteroaryl compounds (see, e.g., B. Crowe and F. Nord. J. Org. Chem. 15, 81 (1950), J. McFarland and H. Howes, J. Med. Chem. 12. 1079 (1969)); Hoffman degradation reaction of 2-(2-thienyl)propyl amide (see, e.g., G. Barger and A. Easson. J. Chem. Soc. 1938, 2100); and amination of 2-(2-thienyl) ethylparatoluenesulfonates, U.S. Pat. No. 4,128,561.

The present method comprises reacting a chiral 2-substituted ethylene oxide derivative with a 2- or 3-yl anion of a heteroaryl compound, and converting, by stereospecific means, the hydroxy group formed in said reaction to an amino group. This method is shown in Reaction Scheme M below.

REACTION SCHEME M

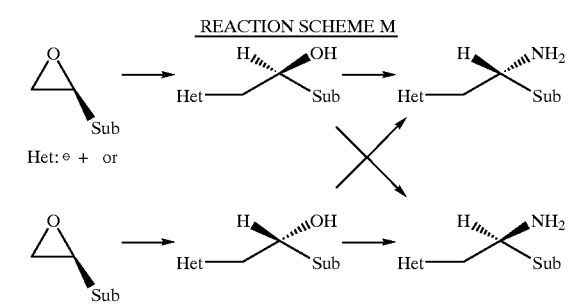

Where Sub represents a substituent group on said chiral ethylene oxide and Het represents a heterocyclic group.

An advantage of this method over methods of preparation of 2-substituted-2-amino-1-(heteroar-2- or 3-yl) ethane derivatives known in the art is that of preparation of a substantially optically pure derivative directly as contrasted with that of a racemic mixture which must then be resolved by other methods to yield the optically pure isomers.

A preferred class of this method is that in which the heteroar-2- or 3-yl group is a substituted or unsubstituted thien-2- or 3-yl or a substituted or unsubstituted benzothiophen-2- or 3-yl group.

A more preferred class of this method is that in which said anion is formed by reacting a substituted or unsubstituted thiophene or benzothiophene having a hydrogen substituent in the 2- or 3-position with an organometallic base in an aprotic organic solvent.

Another more preferred class of this method is that in which said chiral 2-substituted ethylene oxide is substituted in the 2-position by a group selected from the group consisting of alkyl, aryl, trihalomethyl, and benzyloxy.

A most preferred class of this method is that in which said organometallic base is an alkyllithium or lithium diisopropylamide, said aprotic organic solvent is tetrahydrofuran, ether, hexane, or a mixture of those solvents, and said chiral 2-substituted ethylene oxide is a 2-alkyl ethylene oxide derivative.

Means for stereospecifically converting a hydroxy group to an amino group are well known in the art (see, e.g., Mitsunobu, Synthesis 1981 (1), 1).

It should be apparent that the (R)- or (S)-2-substituted-2-hydroxy-1-heteroarylethane derivative may be formed directly as described above by use of the corresponding (S)- or (R)-2-substituted ethylene oxide derivative as the starting material or, if desired or necessary, a resulting (R) or (S)-2-substituted-2-hydroxy-1-heteroarylethane could be converted to the corresponding (S) or (R)-2-substituted-2-hydroxy-1-heteroarylethane derivative, respectively, by means, well known in the art, for inverting the configuration at the hydroxy group (see, e.g. Mitsunobu, Synthesis 1981 (1), 1).

A specific embodiment of this method is that in which: (a) a substituted or unsubstituted thiophene or benzothiophene having a hydrogen substituent in the 2- or 3-position is treated with butyllithium in a mixture of tetrahydrofuran and hexanies at a reduced temperature, for example about −30° C., for a time sufficient to form the anion of said thiophene or benzothiophene; (b) thereafter an (S) or (R) 2-alkyl ethylene oxide is added and the mixture held at a higher temperature, for example about 0° C., for a time sufficient to form the corresponding (R) or (S) 2-alkyl-2-hydroxy-1-thienyl or benzothiophenyl ethane derivative; and (c) thereafter converting, by a stereospecific means, the hydroxy group of said ethane derivative to an amino group.

This method is further illustrated and explained by Examples 50 through 74 hereinbelow.

Examples 1–3 describe the preparation of precursor compounds used in the preparation of compounds of Formula I which are described below.

EXAMPLE 1

Preparation of 6-Chloro-2',3'-dimethyl-methylenedioxy-N-5'-ethyl Carboxamido Adenosine Step 1: 2',3'-dimethylmethylene Derivative of 6-chloropurine Riboside 6-Chloropurine riboside (31.5 g), triethylorthoformate (73 mL) and TsOH (19.8 g) are stirred in 600 ml acetone for 2 hours at RT. The reaction mixture is concentrated in vacuo, combined with ethyl acetate and washed with saturated $NaHCO_3$ solution, and brine, dried ($Na_2SO_4$) and concentrated to yield the 2',3'-dimethylmethylene derivative of 6-chloropurine riboside as a white solid.

Step 2: 6-Chloro-2',3'dimethylmethylenedioxy Adenosine-5'-carboxylic Acid

The product of Step 1 (10 g) is subjected to a Jones oxidation. The acid extracted from ethyl acetate with 2.5% NaOH solution, and the aqueous portion washed with ethyl acetate and acidified with concentrated HCl and extracted with ethyl acetate. The organic layer is washed with $H_2O$ and brine, dried ($Na_2SO_4$), filtered and concentrated in vacuo to dryness, yielding the desired 5'-carboxylic acid.

Step 3: 6-Chloro-2',3-dimethylmethylenedioxy-N-5'ethyl Carboxamido Adenosine

The product from Step 2 (5.7 g) is stirred with BOP-Cl (Bis-(2-oxo-3-oxazoladinyl) phosphinic chloride) (4.26 g) and triethylamine (2.33 mL) in 100 ml methylenle chloride for 20 min at RT. Ethylamine (3.46 g) is stirred into the solution which is stirred for 2 hours at RT. The organic portion is washed with diluted HCl solution, dilute NaOH, $H_2O$, brine and dried ($Na_2SO_4$) to yield the final product as a foam.

EXAMPLE 2

Preparation of (+)-2S-[2a,3a-dimethylmethylenedioxy]-4β-[6-chloro-9-adenyl] cyclopentane-1-β-N-ethyl Carboxamide Step 1: 5,6-Dimethylenedioxy-2-azabicyclo[2.2.1]heptan-3-one 5,6-Dihydroxy-2-azabicyclo[2.2.1]heptan-3-one (23.5 g), (Aldrich) or prepared according to the procedure of Cermak and Vince, Nucleic Acid Chemistry, Improved and New Synthetic Procedures, Methods and Techniques, Part Three, page 26 (J. Wiley 1986), is dissolved in acetone (150 mL) containing 2,2-dimethoxypropane, (185 mL) and p-toluenesulfonic acid (5.25 g), and the mixture is refluxed for 10 min, cooled, treated with $NaHCO_3$ (9.3 g) and concentrated in vacuo. The residue is dissolved in $CH_2Cl_2$, washed with brine, dried over $MgSO_4$ and the solvent evaporated to yield a oil. The oil is chromatographed $SiO_2$ (4:1, ethyl acetate hexane) to give 17.0 g (63%) of a tan white solid. (mp 153–154° C.).

Step 2: (+)-4β-amino-2a,3a-dimethylenedioxycyclopeitane-1β-N-ethyl Carboxamide (A) 5,6-Dimethylenedioxy-2-azabicyclo[2.2.1]heptan-3-one (5 g), prepared in Step 1, is treated with ethylamine (15 mL) at 140° C. for about 7 hours. The resulting product is purified by flash chromatography ($CH_2Cl_2/CH_3OH$/N,N-dimethyl ethylamine, (90/7/3) to yield (±)4β-amino-2a,3a-dimethylenedioxy cyclopentane-1β-ethylcarboxamide (5.8 g).

(B) Treatment of the racemic amine (13.1 g), prepared as described in part A, with D-dibenzoyltartaric acid (21.6 g) affords 15.1 g of an enantiomerically pure salt, $[a]_D$RT=+ 70.1 (C. 1.77, $CH_3OH$). The salt is dissolved in 10% aqueous NaOH and the aqueous phase is extracted with ethyl acetate. The combined organic layers are washed with brine, dried over $MgSO_4$ and the solvent removed to afford the optically pure compound. $[a]_D$RT+31.4 [C. 1.40, MeOH].

Step 3: 4-β-(3-amino-4-chloro-2-pyrimidinylamino)-2,3-dimethylene-dioxycyclopentane-1β-N-ethyl-carboxamide Condensation of (+) 4β-amino-2a,3a-dimethylenedioxycyclopentane-1β-N-ethyl carboxamide (2.10 g), prepared in Step 2, part B, with 3-amino-2,4-dichloropyridine (1.5 g) in n-butanol (70 mL) containing triethylamine (3 mL) for about 14 hours at reflux followed by removal of solvent in vacuo affords an oil which is dissolved in ethyl acetate and washed with aqueous $NaHCO_3$. The organic extract is dried over $Na_2SO_4$ and concentrated in vacuo to yield the optically pure compound. $[a]_D$RT=+15.8 (C.41 .48, $CH_3OH$).

Step 4: (+)-4β-(3-amino-4-chloro-2-pyrimidiiylamino)2a, 3a-dimethylene dioxycyclopentane (2.10 g), formamidine acetate (1.85 g) in methoxyethanol (2 mL) and dioxane (80 mL) are stirred at 70° C. for about 3 hours. The mixture is cooled to room temperature and the solvent removed in vacuo. The residue is dissolved in ethyl acetate which is washed with aqueous $NaHCO_3$ and brine, the organic extract is dried over $Na_2SO_4$, concentrated in vacuo and purified by flash column chromatography (methylene chloridelmethanol 95:5) to yield pure (+)-[2a,3a-dimethylmethylenedioxy]-4β-[6-chloro-9-adenyl]cyclopentane-1β-N-ethyl carboxamide (1.45 g).

Alternatively, optically pure 2a,3a-diprotected dioxy-4β-6-substituted-9-adenyl-cyclopentane-1β-N-ethyl carboxamide derivatives can be prepared by the reaction scheme exemplified in Example 3.

EXAMPLE 3

Preparation of 2S-[2a,3a-cyclohexylidene dioxy]-4β-[N6-(2-thienethan-2-yl)-9-adenyl]cyclopentane-1β-N-ethyl carboxamide Step 1: 4β-ethylene-2a3a-[cyclohexylidenedioxy] cyclopentanone (−)-2a3a-[Cyclohexylidenedioxy]-4-cyclopentenone, (2.95 g), prepared following the procedure of Borchardt et. al. J. Org. Chem. 1987, 52, 5457, is added as a solution in THF (5 mL) to a mixture of vinyl magnesium bromide (15.2 mmol) and CuI (15.2 mmol) in THF (100 mL). This mixture is maintained at −78° C. under an inert atmosphere for about 2 hours, warmed to 0° C. and quenched with saturated aqueous $NH_4Cl$. The organic phase is washed with brine, dried over $MgSO_4$ and concentrated in vacuo to leave a yellow oil, which is purified by flash chromatography (methylene chloride, 100%) to yield 2.9 g of the desired compound as an oil.

Step 2: 4β-ethylene-1-β-hydroxy-2a,3a-[cyclohexylidenedioxy]cyclopentane 3.95 ml of a 1M solution of diisobutyl aluminum hydride in Tetrahydrofuran is added to a solution of THF (75 mL) and ketone prepared in Step 1 (0.73 g), which is cooled to −78° C. The mixture is warmed to −40° C. for about 2.5 hours, treated with 2N NaOH (5mL), warmed to room temperature and stirred for about 1.5 hours. The aqueous phase is extracted with diethyl ether, and the combined organic phases are washed with brine, dried over $MgSO_4$ and concentrated in vacuo to a yellow oil which is purified by flash column chromatography (methylene chloride/methanol, 95:5) to yield 0.65 g of pure product as a viscous oil.

Step 3: 4β-ethylene-1β-trifloromethanesulfonyl-2,3-[cyclohexylidenedioxy]cyclopentane A solution of 4βethylene-1β-hydroxy-2a,3a-[cyclohexylidenedioxy]-cyclopentane (0.65 g) in methylene chloride (5 mL) and pyridine (0.24 mL) is added to a stirred solution of trifluoromethyl sulfonyl anhydride (0.49 mL) in methylene chloride (25 mL) at 0° C. under argon. After about 20 min., brine is added to the reaction mixture, the organic phase is dried over $Na_2SO_4$ and the solvent is removed in vacuo to yield the desired product as an orange oil, which is used without further purification.

Step 4: 1-β-ethylene-[2a,3a-cyclohexylidenedioxy]-4-β-[N6-(2-thienylethane-2-yl)9-adenyl]cyclopentane A solution of N6-thiophenylethyl purine (2.13 g), NaH (50% oil dispersion, 0.35 g) and 18-crown-6 (0.15 g) in DMF (60 mL) is added to a solution of 4β-ethylene-1β-trifluoromethylsulfonyl-2a,3a-[cyclohexylidenedioxy]cyclopentane, prepared in Step 4, in DMF (2 mL) at 0° C. The mixture is stirred at 0° C. for about 8 hours, quenched with saturated $NH_4Cl$, the solvent removed in vacuo, and the residue combined with ethyl acetate (100 mL) and brine. The organic layer is dried over $MgSO_4$, and concentrated in vacuo, and the crude product purified by flash chromatography (methylene chloride/methanol (99:1)) to yield 0.85 g of pure product.

Step 5: 2S[2a,3a-cyclohexylidenedioxyl-4β-[N6-(2-thienylethan-2-yl)-9-adenyl]cyclopentane-1β-N-ethyl Carboxamide A solution of 1β-ethylene-[2a,3a-cyclohexylidenedioxy]-4-β-[N6-(2-thienylethane-2-yl)-9-adenyl]cyclopentane (0.32 g) in 2 ml of benzene is added to a benzene solution of potassium permanganate (0.29 g) and 18-crown-6 (0.016 g) at 0° C. The reaction mixture is maintained at room temperature for about 6 hours, 5% aqueous NaOH (15 mL) added and the aqueous phase filtered through Celite®, and acidified to pH 5 with 1N HCl, and extracted with ethyl acetate. The organic extracts is dried over $MgSO_4$ and concentrated in vacuo to yield 0.1 g of [2a,3a-cyclohexylidenedioxy]-4β-[N-6-(2-thienylethan-2-yl)-9-adenyl]cyclopetane-1-β-carboxylate as a yellow oil which is dissolved in methylene chloride (4 mL) containing dicyclohexyl carbodiimide (DCC) (0.044 g). Ethylamine (0.4 mL) is added to the mixture which is allowed to stir at room temperature for about 18 hours, the solvent removed in vacuo and the crude product purified by flash chromatography (methylene chloridelmethanol 98:2) to yield 0.077 g of pure product.

EXAMPLE 4

Preparation of N6-[trans-2-(thiophen-2-yl)cyclohex-4en-yl]adenosine

Trans-2-(2'-thiophenyl)-cyclohex-4-enylamine (0.3 g) prepared according to method described in Example C, above, 6-chloropurine riboside (0.28 g) and triethylamine (0.27 mL) in 20 ml ethanol are heated to reflux overnight under argon. The reaction mixture is cooled to RT, the solvent removed, and the residue purified by MPLC (chloroform:methanol: 95:5), followed by drying in vacuo at approximately 80° C., to yield the final product as a solid, M.P. 105–110° C.; elemental analysis, $C_{20}H_{23}N_5O_4S$.

EXAMPLE 5

Preparation of N6-[trans-2-(thiophen-2-yl)cyclohexfen-4en-1-yl]adenosine-5'-N-ethylcarboxmide Step 1: (+)Trans-2-(thiophen-2-yl)cyclohex-4-enylamine and the 2',3'-dimethylmethylenedioxy derivative of 6-Cl-NECA are reacted under the conditions described in Example 4, to yield the 2',3'-dimethylmethylenedioxy derivative of the final product.

Step 2: The 2',3'-dimethylmethylenedioxy derivative of the desired product is mixed with trifluoroacetic acid/water (90/10) for 30 min at RT, is neutralized by slowly pouring the mixture into a saturated sodium bicarbonate solution, and is extracted with methylene chloride. The aqueous layer is extracted with methylene chloride and the organic layers combined, washed with brine, dried over magnesium sulfate and filtered, and the filtered clear solution evaporated. The residue is purified by flash chromatography (methylene chloride:methanol 9:1) to yield, upon drying in vacuo, the final product as a white glassy foam, M.P. 112–117° C.; $C_{22}H_{26}N_6O_4S$.

EXAMPLE 6

Preparation of (−)-[2S-[2a,3a-dihydroxy-4-β-[N6-[2-(5-chloro-2-thienyl)-(1R)-1-methylethyl]amino]-9-adenyl]cyclopentane]-1-β-N-ethylcarboxamide Step 1: Optically pure (+)-[2S-[2a,3a-dimethylmethylenedioxy]-4-β(6-chloro-9-adenyl)]cyclopentane-1-β-N-ethylcarboxamide, prepared as described in Example 2, and 2'R-(5-chlorothien-2-yl)-2-propyl amine, $[a]_DRT=-15.6$ (C. 3.7. $CH_3OH$), prepared as described in Example 4, are combined as described in Example 4 affording the 2.3-dimethylmethylenedioxy derivative of the final product.

Step 2: The dimethylmethylenedioxy derivative of step (1) is heated in 5 ml of 50% aqueous formic acid to reflux for about 3 hours. The cooled reaction mixture is evaporated, toluene added to the solid residue and the solvent evaporated. The residue is dissolved in ethyl acetate, washed with sodium bicarbonate solution and brine, dried, filtered, and evaporated to give, after oven drying overnight, a white solid product (0.240 g), M.P. 188–4° C.; $C_{20}H_{25}N_6SO_3Cl$, $[a]_DRT=-86.49$ (C. 5.5. MeOH).

EXAMPLES 7–29, 31–34

Following the general procedures of Examples 1 to 6 above, the compounds set forth in Table 1 are prepared. In Examples 7 through 21, 31 and 32, the heterocyclic amine is reacted with commercially available 6-chloropurine riboside; in Examples 22 and 23, the heterocyclic amine is reacted with N6-chloro-5'-N-ethylcarboxamidoadenosine; and in Examples 24 through 31, 33 and 34, the heterocyclic amine is reacted with either (±) or (+)-[2S-[2a 3 a-dimethylmethylenedioxy-4-β-(6-chloro-9-adenyl)-cyclopentane-1-β-N-ethylcarboxamide.

TABLE I

| Example/RXN Scheme | Amine | Product | M.P./°C. |
|---|---|---|---|
| 7 (F) | (trans-2-thiophen-2-yl-cyclohexylamine) | N[6]-[trans-2-(thiophen-2-yl)-cyclohex-1-yl]adenosine | 165–170 |
| 8 (F) | (trans-2-thiophen-3-yl-cyclohex-4-enylamine) | N[6]-[trans-2-(thiophen-3-yl)-cyclohex-4-en-1-yl]adenosine | 99–105 |
| 9 (C) | (N-(2-aminoethyl)benzothiazol-2-amine) | N[6]-[2-(2'-aminobenzothiazolyl)ethyl]adenosine | 218–219 |
| 10 (C) | (2-(benzothiazol-2-ylthio)ethylamine) | N[6]-[2-(2'-thiobenzothiazolyl)ethyl]adenosine | 149–150 |
| 11 (C) | (2-(6-ethoxybenzothiazol-2-ylthio)ethylamine) | N[6]-[2-(6'-ethoxyl-2'-thiobenzothiazolylethyl]adenosine | 154–155 |
| 12 (H) | (2-(4-methylthiazol-5-yl)ethylamine) | N[6]-[2-(4'-methylthiazol-5'-yl)ethyl]adenosine | 202–203 |
| 13 (G) | (2-(thiazol-2-yl)ethylamine) | N[6]-[2-(2'-thiazolyl)ethyl]adenosine | 181–183 |
| 14 (H) | (2-(2-methylthiazol-4-yl)ethylamine) | N[6]-[2-(2'-methyl-4'-thiazolyl)ethyl]adenosine | 116–118 |
| 15 (D) | ((R)-1-methyl-2-(benzo[b]thiophen-2-yl)ethylamine) | N[6]-[(R)-1-methyl-2-(2'benzo[b]-thiophenyl)ethyl]adenosine[a] | 133–134 |
| 16 (G) | (2-(4-phenylthiazol-2-yl)ethylamine) | N[6]-[2-(4'-phenyl-2'-thiazolyl)ethyl]adenosine | 124–126 |
| 17 (I) | (2-methyl-2-(thiophen-2-ylmethyl)propan-2-amine) | N[6]-[2-(1,1-dimethyl-2'-thiophenyl)ethyl]adenosine | 172–176 |

TABLE I-continued

| Example/RXN Scheme | Amine | Product | M.P./° C. |
|---|---|---|---|
| 18 (G) | 4-methyl-thiazol-2-yl-methylamine | $N^6$-[2-(4'-methyl-2'-thiazolyl)-methyl]adenosine | 104–105 |
| 19 (G) | 4-phenyl-thiazol-2-yl-methylamine | $N^6$-[4-phenyl-2-thiazolyl)-methyl]adenosine | 137–139 |
| 20 (D) | 1-(thiazol-2-yl)propan-2-amine | $N^6$-[1-(thiazol-2-yl)prop-2-yl]-adenosine | 99–106 |
| 21 (D) | 1-(5-chlorothien-2-yl)butan-2-amine | $N^6$-[1-(5"-chlorothien-2"-yl)-2-butyl]adenosine | 135–136 |
| 22 (F$^d$) | trans-2-(thiophen-2-yl)cyclohex-4-en-1-amine | $N^6$-[trans-2-(thiophen-2-yl)-cyclohex-4-en-1-yl]adenosine-5-N-ethyl carboxamide$^b$ | 108–112 |
| 23 (C$^d$) | 2-(benzothiazol-2-ylamino)ethylamine | $N^6$-[2-(2'-(aminobenzothiazolyl)ethyl]adenosine-5-N-ethyl carboxamide | 123–124 |
| 24 (H) | 2-(4-methylthiazol-5-yl)ethylamine | (±)-$N^6$-[2-(4"-methyl-5"-thiazolyl)ethyl]carbocyclic adenosine-5'-N-ethyl carboxamide | 92–93 |
| 25 (G) | 2-(thiazol-2-yl)ethylamine | (±)-$N^6$-[2-(2"-thiazolyl)ethyl]-carbocyclic adenosine-5'-N-ethyl carboxamide | 170 |
| 26 | 2-(thiophen-2-yl)ethylamine | (−)-$N^6$-[(thiophen-2"-yl)ethan-2-yl]carbocyclic adenosine-5'-N-ethyl carboxamide | 185–187 |
| 27 (D) | 1-(thiophen-2-yl)propan-2-amine | (−)-$N^6$[(R)-1-(thiophen-2-yl)prop-2-yl]carbocyclic adenosine-5'-N-ethyl carboxamide$^c$ | 85–87 |
| 28 (E) | 2-(thiophen-3-yl)ethylamine | (±)-$N^6$-[1-(thiopen-3-yl)ethan-2-yl]carbocyclic adenosine-5'-N-ethyl carboxamide | 195–198 |

TABLE I-continued

| Example/RXN Scheme | Amine | Product | M.P./° C. |
|---|---|---|---|
| 29 (C) | 2-(benzothiazol-2-ylamino)ethylamine | (±)-N[6]-[2-(2'-aminobenzothiazolyl)ethyl]carbocyclic adenosine-5'-N-ethyl carboxamide | 209–211 |
| 31 (D) | 1-(3-chlorothien-2-yl)butan-2-amine | N[6]-[1-ethyl-2-(3-chlorothien-2-yl)ethyl]adenosine | 137–139 |
| 32 (D) | 1-(3-chlorothien-2-yl)propan-2-amine | N[6]-[1-methyl-2-(3-chlorothien-2-yl)ethyl]adenosine | 137–139 |
| 33 (D) | 1-(3-chlorothien-2-yl)butan-2-amine | (−)-[2S-[2a,3a-dihydroxy-4b-[N[6]-[2-(3-chloro-2-thienyl)-1(R,S)-ethylethyl]amino]-9-adenyl]cyclopentane-1b-ethyl carboxamide | 88–91 |
| 34 | 1-(3-chlorothien-2-yl)butan-2-amine | (−)-[2S-[2a,3a-dihydroxy-4b-[N[6]-[2-(3-chloro-2-thienyl)-1(R)-ethylethyl]amino]-9-adenyl]cyclopentane-1b-ethyl carboxamide | 95–96 |

[a] optical rotation of alcohol precursor of amine: $[\alpha]^{RT}$ = +14.9° (C.1.27, CH$_3$OH)
[b] optical rotation of amine: $[\alpha]^{RT}$ = +25.8° (C.1.67, CH$_3$OH)
[c] optical rotation: $[\alpha]^{RT}$ = −15.6° (C.3.04, CH$_3$OH)
[d] amine reacted with 2',3'-isopropylidene derivative of N[6]-chloro-5'-N-ethylcarboxamide adenosine; deprotection according to procedure of Example 11.

EXAMPLE 30

Preparation of (±)-N6-[1-(thiopheny-2-yl)ethan-2-yl]-N'-1-deazaaristeromycin-5'-N-ethyl Carboxamide Step 1: 2-chloro-3-nitro-4-[2-(2-thiophenyl)ethyl] aminopyridine A mixture of 2,4-dichloro-3-nitropyridine (1.5 g), 2-aminoethylthiophene (1 g) and triethylamine (5 mL) is heated to reflux in EtOH (60 mL). The reaction mixture is cooled, the solvent evaporated and the residue chromatographed on silica gel (10% hexane/CH$_2$Cl$_2$) to yield the desired addition product.

Step 2: (±)1β-N-ethyl carboxamide-2a,3a-isopropylidenedioxy-4β-[2-(3-nitro-4-[2-(2-thiophenyl)ethyl]aminopyridyl)amino]cyclopentane A mixture of the thiophenylamino pyridine of step (1) (1.8 mmol), (±)-1β-N-ethyl carboxamide-4β-amino-2a,3a-isopropylidenedioxycyclopentane (0.3 g) and triethylamine (0.3 mL) is heated to reflux in nitromethane (15 mL) for about 5 hours. The solvent is removed and the residue taken up in methylene chloride. chromatographed on silica gel (2% methanol/chloroform) affording a solid product which is used as is in the next step.

Step 3: (±) 1β-N-ethyl carboxamide-2a,3a-isopropylidenedioxy-4β-[2-(3-amino-4-[2-(2-thiophenyl)ethyl]aminopyridyl)amino]cyclopentane A mixture of the nitro compound of step (2) (0.39g). Pd/C (0.01 g) in ethanol (7 mL) is stirred under a hydrogen atmosphere for about 5 hours. The catalyst is filtered and the filtrate evaporated affording an oil which is purified on Florsil (10% methanol/methylene chloride) to yield the desired product as a solid.

Step 4: (±) -N6-[1-(thiopheny-2-yl)ethan-2-yl]-N'-1-deazaaristeromycin-5'-N-ethyl Carboxamide A mixture of the amino compound of step (3) (0.31 g) and formamidine acetate (0.72 g) in methoxyethanol (30 mL) is heated to reflux for about 3 hours. The reaction mixture is cooled, the solvent evaporated and water (5 mL) and formic acid (5 mL) added to the residue. The acidic mixture is heated to 50° C. for about 5 hours, after which the solvent is removed and the residue chromatographed on silica gel (10% methanol/methylene chloride) yielding an oil which is recrystallized from ethyl acetate to the desired product as a crystalline solid. M.P.=155–156° C.

The optically pure compound is prepared using the + or − enantiomer of the cyclopentane amine in Step (2).

EXAMPLE 35

Preparation of (2S)-2a,3a-dihydroxy-4β-[N6-[2-(5-chloro-2-thienyl)-(1R)-1-methylethyl]amino-9-adenyl]cyclopentane-1β-N-ethylcarboxamide-N[1]-oxide A solution of 2S-2a,3a-dihydroxy-4β-[N6-[2-(5-chloro-2-thienyl)-(1R)-1-methylethyl]amino-9-adenyl]cyclopentane-1β-N-ethylcarboxamide (0.25 g) and glacial acetic acid (20 mL) in 30% hydrogen peroxide (1 L) is stirred for 4 days at room temperature and the mixture concentrated in vacuo. The residue is purified by flash chromatography, eluting with 20% methanol in ethyl acetate, followed by stirring with hot methanol and filtering to give the desired product, m.p.>240° C.

EXAMPLE 36

Preparation of [1S-[1a,2b,3b,4a(S*)]]-4-[7-[[2-(5-chloro-2-thienyl)-1-methylethyl]amino]-3H-imidazo [4,5-b]pyridin-3-yl]-N-ethyl-2,3-dihydroxycyclopentanecarboxamide Step 1: Preparation of 2-chloro-4-[2-(5-chloro-2-thienyl)-(1R)-1-methylethyl]amino-3-nitropyridine Using essentially the procedure of Example 30, Step 1, and purifying the crude product by flash chromatography, eluting with gradient of 10% to 30% ethyl acetate in heptane, the desired product is prepared from 2-(5-chloro-2-thienyl)-(1R)-1-methylethylamine.

Step 2: Preparation of (−)-1β-N-ethyl-2a,3a-isopropylidenedioxy-4β-[4-[2-(5-chloro-2-thienyl)-(1R)-1-methylethyl]amino-3-nitro-2-pyridyl]amino-cyclopentanecarboxamide 2-chloro-4-[2-(5-chloro-2-thienyl)-(1R)-1-methylethyl]amino-3-nitropyridine (0.68 g), (−)-1b-N-ethyl-2a,3a-isopropylidendioxy-4b-aminocyclopentanecarboxamide (0.381 g), and triethylamine (0.85 mL) are combined in ethanol (50 mL) and the mixture heated at reflux for about 18 hours. The mixture is concentrated in vacuo and the crude product purified by flash chromatography eluting with 0.5% methanol in methylene chloride to give the desired product.

Step 3: Preparation of (−)-1β-N-ethyl-2a,3a-isopropylidenedioxy-4β-3-amino-[2-5-chloro-2-thienyl)-(1R)-1-methylethyl]amino-2-pyridyl]amino-cyclopentanecarboxamide (−)-1β-N-ethyl-2a,3a-isopropylidenedioxy-4β-[4-[2-(5-chloro-2-thienyl)-(1R)-1-methylethyl]amino-3-nitro-2-pyridyl]aminocyclopentanecarboxamide (0.9 g), and tin(II) chloride dihydrate (2.1 g) are combined in ethanol (20 mL) and the mixture heated at 70° C. for about 30 minutes. The mixture is poured over ice, made slightly alkaline with aqueous sodium bicarbonate, and the aqueous extracted with ethyl acetate. The ethyl acetate solution is dried over magnesium sulfate, filtered, and concentrated in vacuo to give the desired product which is used, without further treatment, for the next step.

Step 4: Preparation of [1S-[1a,2b,3 b,4a(S*)]]-4-[7-[[2-(5-chloro-2-thienyl)-1-methylethyl]amino]-3H-imidazo[4,5-b] pyridin-3-yl]-N-ethyl-2,3-dihydroxycyclopentanecarboxamide Using essentially the procedure of Example 30, Step 4, the desired product. m.p. 164–165° C. is prepared from (−)-1β-N-ethyl-2a,3a-isopropylidenedioxy-4β-[3-amino-4-[2-(5-chloro-2-thienyl)-(1R)-1-methylethyl]amino-2-pyridyl]amino-cyclopentanecarboxamide.

Using essentially the procedures of Example 30, the compounds of Examples are prepared from the appropriate starting materials.

EXAMPLE 37

[1S-[1a,2b,3b,4a]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide, m.p. 79–82° C.

EXAMPLE 38

[1S-[1a,2b,3 b,4a]]-4-[7-[[2-(2-thienyl)-1-isopropylethyl]amino]-3H-imidazo[4,5-b]pyridin-3-yl]-N-ethyl-2,3-dihydroxycyclopentanecarboxamide, m.p. 75–85° C.

EXAMPLE 39

[1S-[1a,2b,3b,4a(S*)]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide. m.p. 75–78° C.

EXAMPLE 40

[1S-[1a,2b,3b,4a(S*)]]-4-[7-[[2-(2-thienyl)-1-methylethyl]amino]-3H-imidazo[4,5-b]pyridin-3-yl]-N-ethyl-2,3-dihydroxycyclopentane-carboxamide, m.p. 155–60° C.

EXAMPLE 41

Preparation of [1S-[1a,2b,3b,4a]]-4-[7-[[2-(5-chloro-2-thienyl)-1-ethylethyl]amino]-3H-imidazo [4,5-b]pyridin-3-yl]-N-ethyl-2,3-dihydroxycyclopentane-carboxamide Using essentially the procedures of Example 36, the desired product, m.p. 77–85° C. is prepared from 2-(5-chloro-2-thienyl)-(1R)-1-ethylethylamine.

EXAMPLE 42

Preparation of (2S)-2a,3a-bis-methoxycarbonyloxy-4β-[N6-[2-(5-chloro-2-thienyl)(1R)-1-methylethyl] amino-9-adenyl]cyclopentane-1βN-ethylcarboxamide To a solution of (2S)-2a,3a-dihydroxy-4β-[N6-[2-(5-chloro-2-thienyl-(1R)-1-methylethyl]amino-9-adenyl] cyclopentane-1β-N-ethylcarboxamide (0.56 g) and triethylamine (0.5 mL) and 4-dimethylaminopyridine (1 mg) in tetrahydrofuran (25 mL) is added methyl chloroformate (0.21 mL) and the solution stirred at room temperature for 1 hour. The mixture is diluted with ethyl acetate, washed with brine, and the organic solution dried over magnesium sulfate, filtered and concentrated in vacuo. The crude product is recrystallized from hexane/ethyl acetate to give the desired product, m.p. 74–76° C.

EXAMPLE 43

Preparation of (2S)-2a,3a-dihydroxy-4β-[N6-[2-(5-chloro-2-thienyl)-(1R)-1-methylethyl]amino-9-adenyl]cyclopentane-1β-N-ethylcarboxamide Ethoxymethylene Acetal A solution of (2S)-2a,3a-dihydroxy-4β-N6-[2-(5-chloro-2-thienyl)-(1R)-1-methylethyl]amino-9-adenyl] cyclopentane-1β-N-ethylcarboxamide (0.14 g), triethylorthoformate (3 mL), and p-toluenesulfonic acid (1 mg) is heated at reflux for about 1 hour and the solvent then removed in vacuo. The residue is dissolved in ethyl acetate and the solution washed with brine, dried over sodium sulfate, filtered, concentrated in vacuo. The crude is purified by flash chromatography, eluting with 5% methanol in methylene chloride, followed by recrystallization from hexane/ethyl acetate to give the desired product, m.p. 67–70° C.

EXAMPLE 44

Preparation of (2S)-2a,3a-dihydroxy-4β-[N6-[2-(5-chloro-2-thienyl)-(1R)-1-methylethyl]amino-9-adenyl]cyclopentane-1β-N-ethylcarboxamide-2,3-carbonate A solution of (2S-2a,3a-dihydroxy-4β-[6-[2-(5-chloro-2-thienyl)-(1R)-1-methylethyl]amino-9-adenyl]cyclopentane-1β-N-ethylcarboxamide (0.17 g) and 1,1'-carbonyldiimidazole (0.071 g) in benzene (5 mL) is refluxed for 5 hours then stirred at 60° C. for about 18 hours. The solution is washed with brine, dried over magnesium sulfate, filtered and concentrated in vacuo. The residue is purified by flash chromatography, eluting with 5% methanol in methylene chloride, followed by crystallization from hexane/ethyl acetate to give the desired product, m.p. 87–89° C.

EXAMPLE 45

Preparation of (2S)-2a,3a-bis-methylcarbamoyloxy-4β-[N6-[2-(5-chloro-2-thienyl-(1R)-1-methylethyl]amino-9-adenyl]cyclopentane-1β-N-ethylcarboxamide To a solution of (2S)-2a,3a-dihydroxy-4β-[N6-[2-(5-chloro-2-thielyl)-(1R)-1-methylethyl]amino-9-adenyl]cyclopentane-1β-N-ethylcarboxamide (0.16 g) in tetrahydrofuran (5 mL) is added methyl isocyanate (0.05 mL) and 1,8-diazabicyclo[5.4.0]undec-7-ene (1 drop). The solution is stirred at 50° C. for about 2.5 hours, cooled to room temperature, diluted with ethyl acetate and washed with brine. The organic solution is washed with brine, dried over magnesium sulfate and concentrated in vacuo. The residue is purified by flash chromatography, eluting with 5% methanol in methylene chloride, followed by crystallization from hexane/ethyl acetate to give the desired product, m.p. 97–99° C.

EXAMPLE 46

Preparation of (2S)-2a,3a-dihydroxy-4β-[N6-[2-(5-chloro-2-thienyl-(1R)-1-methylethyl]amino-9-adenyl]cyclopentane-1β-N-ethylcarboxamide-2,3-thiocarbonate A solution of (2S)-2a,3a-dihydroxy-4β-[N6-[2-(5-chloro-2-thienyl)-(1R)-1-methylethyl]amino-9-adenyl]cyclopentane-1β-N-ethylcarboxamide (0.35 g) and thiocarbonyldiimidazole (0.134 g) in benzene (10 mL) is heated at 45° C. for about 2 hours. The solution is washed with brine, dried over magnesium sulfate, and concentrated in vacuo. The residue is purified by flash chromatography, eluting with 5% methanol in hexane, followed by crystallization from hexane to give the desired product, m.p. 115–117° C.

EXAMPLE 47

Preparation of $N^6$-[2-(3-chloro-2-thienyl)-(1R)-1-methylethyl]-2'-O-methyladenosine A solution of 6-chloro-9-(2'-O-methyl-b-D-ribofuranosyl)-9H-purine (prepared as in EP Publication No. 0378518) (0.28 g), 2-(3-chloro-2-thienyl)-(1R)-1-methylethylamine (0.163 g), and triethylamine (0.5 mL) in ethanol (30 mL) is refluxed for about 18 hours, cooled and concentrated in vacuo. The residue is purified by flash chromatography, eluting with 10% methanol in methylene chloride, followed by crystallization from hexanelethyl acetate, to give the desired product, m.p. 75–76° C.

EXAMPLE 48

Preparation of $N^6$-[2-(5-chloro-2-thienyl)-(1R)-1-methylethyl]-2'-O-methyladenosine Using essentially the procedure of Example 47, the desired product. m.p. 84–85° C., is prepared from 2-(5-chloro-2-thienyl)-(1R)-1-methylethylamine.

EXAMPLE 49

Preparation of $N^6$-[trans-5-(2-thienyl)cyclohex-1-en-4-yl]-2'-O-methyladenosine Using essentially the procedure of Example 47, the desired product, m.p. 86–89° C., is prepared from trans-2-(2-thienyl)cyclohex-4enylamine.

EXAMPLE 50

Preparation of 1(R)-2-(5-chloro-2-thienyl)-1-methylethylamine

Step 1: Preparation of 1(S)-2-(5-chloro-2-thienyl)-1-hydroxy-1-methylethane

A solution of 2-chlorothiophene (8.17 g) in tetrahydrofuran (80 mL) is cooled to −30° C. and 1.6M n-butyllithium in hexanes (43.0 mL) is added dropwise. The mixture is stirred at −30° C. for about 1 hour, (S)-propylene oxide (4 g) is added, and the mixture is warmed to 0° C. and stirred at that temperature for about 3 hours. The reaction is quenched with saturated aqueous ammonium chloride solution, diluted with ether, and the layers separated. The organic layer is washed with brine, dried over magnesium sulfate, and concentrated in vacuo to give the desired product.

Step 2: Preparation of 1(R-2-(5-chloro-2-thienyl)-1-methyl-1-phthalimidoethane

To a solution of 1(S)-2-(5-chloro-2-thienyl)-1-hydroxy-1-methylethane (8.8 g), triphenylphosphine (13.1 g), and phthalimide (7.35 g) in tetrahydrofuran (80 mL) is dropwise added diethyl azodicarboxylate (7.9 mL). The solution is stirred for about 18 hours and the solvent removed in vacuo. The residue is purified by flash chromatography, eluting with 20% hexanes in methylene chloride, to give the desired product.

Step 3: Preparation of 1(R)-2-(5-chloro-2-thienyl)-1-methylethylamine

1(R)-2-(5-chloro-2-thienyl)-1-methyl-1-phthalimidoethane (13 g) is dissolved in ethanol (75 mL) and hydrazine hydrate (2.5 mL) is added and the mixture stirred at reflux for about 1 hour. The mixture is cooled to room temperature, the solid removed by filtration, and the filtrate concentrated in vacuo. The residue is dissolved in ethyl acetate and this solution stirred with 5N aqueous hydrochloric acid. The layers are separated and the aqueous adjusted to ph>10 with 10% sodium hydroxide solution, then extracted with ethyl acetate. The organic solution is washed with brine, dried over magnesium sulfate, filtered, and concentrated in vacuo to give the desired product, $[a]_D$=−22.96° (c=11.5, methanol).

EXAMPLE 51

Preparation of 1(R)-2-(2-thienyl)-1-methylethylamine

Step 1: Preparation of 1(S)-2-(2-thienyl)-1-hydroxy-1-methylethane

Using essentially the procedure of Example 50, Step 1, the desired product is prepared from thiophene.

Step 2: Preparation of 1(R)-2-(2-thienyl)-1-methyl-1-phthalimidoethane

Using essentially the procedure of Example 50, Step 2, the desired product is prepared from 1(S)-2-(2-thienyl)-1-hydroxy-1-methylethane.

Step 3: Preparation of 1(R)-2-(2-thienyl)-1-methylethylamine

Using essentially the procedure of Example 50, Step 3. the desired product $[a]_D=-15.6°$ (c=1, methanol) is prepared from 1(R)-2-(2-thienyl)-1-methyl-1-phthalimidoethane.

EXAMPLE 52

Preparation of 1(S)-2-(5-chloro-2-thienyl)-1-methylethylamine

Step 1: Preparation of 1(S-2-(5-chloro-2-thienyl)-1-hydroxy-1-methylethane

To a stirred solution of 1(S)2-(5-chloro-2-thienyl-1-hydroxy-1-methylethane (5.7 g) in tetrahydrofuran (100 mL) is added triphenylphosphine (5.34 g) and benzoic acid (2.49 g). Diethyl azodicarboxylate (3.22 mL) is added dropwise and the mixture stirred at room temperature for about 18 hours. The solvent is removed in vacuo. The residue is purified by flash chromatography, eluting with 30% hexanes in methylene chloride, to give (R)-3-(5-chloro-2-thienyl)-2-propyl benzoate. The ester (3.91 g) is dissolved in dioxane (50 mL) and 20% aqueous sodium hydroxide (15 mL) is added. The mixture is heated at 55° C. for 3 hours and concentrated in vacuo. The residue is taken up in ethyl acetate (200 mL) and the organic layer washed with brine, dried over magnesium sulfate, filtered, concentrated in vacuo to give the desired product.

Step 2: Preparation of 1(S)-2-(5-chloro-2-thienyl)-1-methylethylamine

Using essentially the procedure of Example 50, Steps 2 and 3, the desired product $a_D=+21.71°$ (c=1.1. methanol) is prepared from 1(S)-2-(5-chloro-2-thienyl)-1-hydroxy-1-methylethane.

Using essentially the procedures of Examples 50, 51, and 52, the following compounds are prepared from appropriate starting materials.

EXAMPLE 53

1(R)-2-(benzothiophen-2-yl)-1-methylethylamine

EXAMPLE 54

1(S)-2-(2-thienyl)-1-methylethylamine, $a_D=15.5°$ (c=1, methanol)

EXAMPLE 55

1(R)-2-(3-bromo-2-thienyl)-1-methylethylamine

EXAMPLE 56

1(R)-2-[5-(2-pyridyl)-2-thienyl]-1-methylethylanine

EXAMPLE 57

1(R)-2-[5-(2-thienyl)-2-thienyl]-1-methylethylamine

EXAMPLE 58

1(R)-2-(5-phenyl-2-thienyl)-1-methylethylamine

EXAMPLE 59

1(R)-2-(5-methoxy-2-thienyl)-1-methylethylamine

EXAMPLE 60

1(R)-2-(5-methyl-2-thienyl)-1-methylethylamine

EXAMPLE 61

1(R)-2-(5-bromo-2-thienyl)-1-methylethylamine

EXAMPLE 62

1(R)-2-(5-iodo-2-thienyl)-1-methylethylamine

EXAMPLE 63

1(R)-2-(5-methylthio-2-thienyl)-1-methylethylamine

EXAMPLE 64

1(R)-2-(5-methylsulfonyl-2-thienyl)-1-methylethylamine

EXAMPLE 65

1(R)-2-(5-ethyl-2-thienyl)-1-methylethylamine

EXAMPLE 66

1(R)-2-(5-n-heptyl-2-thienyl)-1-methylethylamine

EXAMPLE 67

1(R)-2-(3-methyl-2-thienyl)-1-methylethylamine

EXAMPLE 68

1(R)-2-(4-methyl-2-thienyl)-1-methylethlylamine

EXAMPLE 69

1(R)-2-(3-chloro-2-thienyl)-1-methylethylamine, $[a]_D=-6.1°$ (c=1, methanol)

EXAMPLE 70

1(R)-2-(4-chloro-2-thienyl)-1-methylethylamine

EXAMPLE 71

1(R)-2-(3-chloro-5-phenyl-2-thienyl)-1-methylethylamine

EXAMPLE 72

1(R)-2-(5-bromo-2-chloro-2-thienyl)-1-methylethylamine

EXAMPLE 73

1(R)-2-(4-methyl-5-chloro-2-thienyl)-1-methylethylamine

EXAMPLE 74

1(R)-2-(2,5-dichloro-3-thienyl)-1-methylethylamine

EXAMPLE 75

A mixture of 13.88 g (29.7 mmol) of the product of Example 37 and 4.27 g (41 mmol) of formamidine acetate in 200 mL of n-BuOAc is refluxed for 1 hour. At this point the reaction is complete as is determinable by HPLC. After cooling, the reaction mixture is washed with 5 wt % NaHCO$_3$ and brine, dried over Na$_2$SO$_4$ and filtered. The filtrate is treated with 13.8 g (59.4 mmol) of (1R)-(−)-10-camphorsulfonic acid to separate a sticky solid. The slurry is taken to reflux to make the precipitate more granular. After cooling, the solid is collected, washed with EtOAc and dried in vacuo to yield 10.41 g of di[(1R)-(−)-camphorsulfonic acid] salt of [1S-[1a,2b,3b,4a,(S*)]]-4-[7-[[2-(3-chloro-2-thienyl)-1-ethylethyl]amino]-3H-imidazo[4,5-b]pyridin-3-yl]-N-ethyl-2,3-dihydroxycyclo-pentanecarboxamide as an off-white powder. The product can be recrystallized (CH$_3$CN) in high recovery and improved purity if desired.

The following analytical data has been generated on a representative sample of di[(1R)-(−)-camphorsulfonic acid) salt of [1S-[1a,2b,3b,4a,(S*)]]-4-[7-[[2-(3-chloro-2-thienyl)-1-ethylethyl]amino]-3H-imidazo[4,5-b]pyridin-3-yl]-N-ethyl-2,3-dihydroxycyclopentanecarboxamide:

Differential Scanning Calorimeter: mp 188°

Elemental Analysis: Calculated: C,53.51; H, 6.42; N, 7.43; Cl, 3.76; S, 10.20; Found: C, 53.41; H, 6.47; N, 7.34; Cl, 4.03; S, 10.07.

EXAMPLE 76

A 3-neck 5 L round-bottomed flask equipped with an overhead stirrer, a temperature probe with a chart recorder and a condenser (chilled with syltherin XLT, at a temperature of 2.6° C.) is charged with dimethyl acetonedicarboxylate (696.6 g, 4 mol), trimethylorthoformate (424.5 g, 4 mol) and acetic anhydride (816.72 g, 8 mol) under a stream of nitrogen. The resulting amber homogenous solution is stirred rapidly (400 rpm) and heated to reflux at a temperature of 115° C. in 40 minutes using a heating mantle. A gentle reflux is maintained by adjusting the heating over the next hour. (The boiling point of the mixture gradually decreases to 95° C. as the reaction progresses). The resulting orange, homogenous mixture is then distilled at maximum a temperature of 115° C. under vacuum (20 mm Hg) using a Claisen head. About 1000 mL of distillate (containing AcOH, and MeOAc) is collected. The dark orange residue is cooled with an ice bath at a temperature of 6° C.) and ammonium hydroxide (1 L, 8 mol) is then added dropwise in order to control the exothermic reaction to a temperature of less than 25° C., total time=1.5 hours. The yellow suspension is acidified with HCl (pH 2.0) (750 mL, 9 mol) and the resulting tan solid is filtered, washed with 1 L MeOH and dried by suction until constant weight. Thus, a first crop of methyl 4,6-dihydroxy nicotinate (351 g, 51%) is obtained with 97% purity. A second crop of methyl 4,6-dihydroxy nicotinate (35 g) may be obtained by halving the volume of the methanolic filtrate.

Mass Spec., 169 (M+, 97%) 137 (100%).

The product is subject to chromatographic analysis by two methods:

HPLC method A: uses Column type, Alitec Absobospliere-SCX, 5μ, 250×4.6 mm; Mobile phase A: 50 mm NaH$_2$PO$_4$, pH=3.5 with H$_3$PO$_4$, B: CH$_3$CN, A:B=95:5; Flow rate, 1.0 mL/minute; Detection, UV absorbance at 210 nm; Retention time, 3.9 minutes. The purity of the product is determined to be 97.8%.

HPLC method B: uses Column type, Sulpeco Sulpecosil-SAX, 5μ, 250×4.6 mm; Mobile phase, A: 200 mm KH$_2$PO$_4$ with 0.1% TEA, pH=6.0 with H$_3$PO$_4$, B: CH$_3$CN, A:B=85:15; Flow rate, 1.0 mL/minute; Detection, UV absorbance at 210 nm; Retention time, 4.9 minutes.

EXAMPLE 77

A 3-neck 2 L flask is equipped with a temperature probe with a chart recorder, mechanical stirrer, a Dean-Stark apparatus and a reflux condenser and charged with methyl 4,6-dihydroxynicotinate (100 g (97% purity), 0.59 mol) and phosphoric acid (85%. 300 mL). The suspension is heated with a heating mantle and at a temperature of 120° C. a burgundy-red solution is obtained (mantle at a temperature of 290° C., elapsed time 1 hour). At a temperature of 140° C. a white precipitate 4,6-dihydroxynicotinic acid appears at once (although methanol is generated, no methanol is observed in the distillate which suggests the formation of a phosphate ester) and from this point on considerable foaming is generated. This foaming is controllable by the addition of a surfactant such as silicon oil 550 (5–6 drops). Water inclusive of that originating from the phosphoric acid is then removed (about 60 mL), e.g., dehydration of the phosphoric acid, until the internal temperature reaches 210° C.±5° C. (mantle at a temperature of 290° C., total elapsed time 2.5 hours). Without the dehydration of the phosphoric acid, the carboxylation does not occur. After stirring for 4–5 hours at that temperature, the disappearance of 4,6-dihydroxynicotinic acid and methyl 4,6-dihydroxynicotinate is confirmed by HPLC. The reaction mixture is then allowed to cool down to a temperature of less than 100° C. at which point acetic acid (300 mL) is added and the temperature is maintained at 90° C. To this mixture is added nitric acid (25 mL) at a constant rate (5–6 mL/minute) until HPLC shows no more 2,4-dihydroxypyridine present. Water (300 L) is then added to the reaction and the heating is stopped. A dark brown solid starts appearing at a temperature of less than 80° C. and is allowed to precipitate with stirring for 2–3 hours. Filtration through a scintered glass funnel (medium porosity) yields a dark brown solid which is then washed with 250 mL of isopropyl alcohol. The resulting cake is air-dried for 1 hour and then put in a drying oven under vacuum (20 in. Hg with air bleed) at 50° C. for 2 days. 2,4-Dihydroxy-3-nitropyridine (60 g) is obtained in 60% yield.

Differential Scanning Calorimeter: mp 183.85° C.: Elemental analysis for C$_5$H$_4$N$_2$O$_4$: calc. C 38.47, H 2.58, N 17.95; found C 38.42, H 2.62, N 17.69: I R, 3194.9 (OH), 1689.2 (C=O), 1616.5 (C=C); Mass Spec. (M+H), 157.

The product is subject to chromatographic analysis by two methods:

HPLC method A: uses Column type, Alltec Absobosphere-SCX, 5μ, 250×4.6 mm; Mobile phase A: 50 mm NaH$_2$PO$_4$, pH=3.5 with H$_3$PO$_4$, B: CH$_3$CN, A:B=95:5; Flow rate, 1.0 mL/minute; Detection, UV absorbance at 210 nm; Retention time, 4.2 minutes. The purity of the product is determined to be 99.92%.

HPLC method B: uses Column type, Sulpeco Sulpecosil-SAX, 5μ, 250×4.6 mm; Mobile phase, A: 200 mm KH$_2$PO$_4$ with 0.1% TEA, pH=6.0 with H$_3$PO$_4$with 0.1% TEA, pH=6.0 with $H_3PO_4$, B: $CH_3CN$, A:B=85:15; Flow rate, 1.0 mL/minute; Detection, UV absorbance at 210 nm; Retention time, 10 minutes.

EXAMPLE 78

A 3-neck 22 L flask equipped with a temperature probe with a chart recorder, mechanical stirrer, a Dean-Stark apparatus and a reflux condenser is charged with 4,6-dihydroxy nicotinic acid (88 %, 2.0 Kg, 12.81 mol), phosphoric acid (85%. 6 L, 103.15 mol). The off gases from the condenser are scrubbed by bubbling into 50% aqueous NaOH. The suspension is heated until a sufficient amount of water has been removed (about 1.2 L), i.e., dehydration of the phosphoric acid. Without the dehydration of the phosphoric acid, the carboxylation does not occur. For the internal temperature to reach 210° C.±5° C., a mantle temperature of 290° C. is applied over an elapsed time of 3.5 hours. After being stirred for 4–5 hours at that temperature, the disappearance of the starting material is confirmed by HPLC. The reaction mixture is then allowed to cool down to a temperature of less than 100° C., at which point acetic acid (6 L, 104.81 mol) is added and the temperature is maintained at 90° C. To this mixture is added nitric acid (485 mL, 12.11 mol) at a constant rate (5–6 mL/minute) until HPLC shows no more 4,6-dihydroxy nicotinic acid present. Water (6 L, 333.3 mol) is then added to the reaction and heating is stopped. A yellow solid starts appearing at a temperature of less than 80° C. and is allowed to precipitate with stirring overnight. Filtration in a scintered glass funnel (course porosity) yields a yellow solid which is then washed with 2.5 L of isopropyl alcohol. The resulting cake is air-dried for 48 hours and then put in a drying oven under vacuum (20 in. Hg with a air bleed) at 50° C. for 3 days. 2,4-dihydroxy-3-nitropyridine (1.050 Kg) is obtained in 60% yield.

Caution: This material exhibits a large exothermic reaction on the onset of melting at 262.62° C. by DSC, it is therefore our recommendation not to heat this substance within 100° C. of its melting point.

Differential Scanning Calorimeter: mp 183.85° C.; Elemental Analysis for $C_5H_4N_2O_4$: calc. C 38.47, H 2.58, N 17.95; found C 38.42, H 2.62, N 17.69; IR, 3194.9 (OH), 1689.2 (C=O), 1616.5 (C=C); Mass Spec., 157 (M=H. 100%).

The product is subject to chromatographic analysis by two methods:

HPLC method A: uses Column type, Alltec Absobosphere-SCX. 5μ, 250×4.6 mm: Mobile phase, A:50 mm $NaH_2PO_4$, pH=3.5 with $H_3PO_4$, B: $CH_3CN$, A:B=95:5; Flow rate, 1.0 mL/minute; Detection, UV absorbance at 210 nm; Retention time, 4.2 minutes. The purity of the product is determined to be 99.92%.

HPLC method B: uses Column type, Sulpeco Sulpecosil-SAX, 5μ, 250×4.6 mm: Mobile phase, A: 200 mm $KH_2PO_4$ with 0.1% TEA, pH=6.0 with $H_3PO_4$, B: $CH_3CN$, A:B= 85:15; Flow rate, 1.0 mL/minute; Detection, UV absorbance at 210 nm; Retention time, 10 minutes.

EXAMPLE 79

2,4-Dihydroxy-3-nitropyridine (590 g; 3.78 mol) is charged into a 3-neck 12 L flask equipped with a temperature probe with a chart recorder, addition funnel, Claisen head, condenser and mechanical stirrer. Off gases from the condenser are scrubbed by bubbling into 50% aqueous NaOH. Stirring of the solid is initiated. $POCl_3$ (1058 mL) is added and the resulting semi-solid is heated to 45° C. to obtain a stirred suspension. To this is added DIPEA (988 mL) over 1 hour. This exothermic reaction is controlled by the rate of addition of diisopropylethylamine (DIPEA). After the addition is complete, the reaction is heated to 100° C.±5° C. Conversion of 2,4-dihydroxy-3-nitropyridine, through the intermediate monochloro compound, is complete after 4 hours (HPLC; Method C). The reaction mixture is then cooled to 20° C. and quenched into ice-water with vigorous stirring. A tan solid precipitates, the ice is allowed to melt and the resulting mixture is filtered through a scintered glass funnel. The product is air-dried overnight and then transferred to a vacuum oven and dried to constant weight (29 in. Hg, 20° C.). 2,4-dichloro-3-nitropyridine is obtained as an off-white solid (699 g, 96% yield).

If the color or purity of the product obtained by the above method is unsatisfactory it may be recrystallized as follows: the solid is transferred into a flask equipped with mechanical stirrer and a dean-stark apparatus. Heptane (5 mL/g) is then added and the mixture is heated to reflux. Any residual water is removed by azeotropic distillation. The solution is filtered through Celite and the filtrate is allowed to cool with stirring and a tan solid is then collected by filtration and air dried to constant weight.

Elemental Analysis for $C_5H_2N_2O_2Cl_2$: calc. C 31.26, H 1.05, N 14.59, Cl 36.44; found C 31.31, H 1.26, N 14.41; Mass Spec., 192 (M+, 90%).

The product is subject to chromatographic analysis by two methods:

HPLC method A is undertaken as described in Example 76 and the purity of the product is determined to be 99.33%.

HPLC method C: uses Column type. MicrosorbMV-C18, 5μ, 250×4.6 mm; Mobile phase, A: $H_2O$ with 0.1% AcOH, B: $CH_3CN$; A:B=70:30; Flow rate, 1.0 mL/min.; Detection, UV absorbance at 220 nm; Retention time, 5.3 minutes.

EXAMPLE 80

2,4-Dihydroxynitropyridine (85 mL, 0.914 mol) is charged to 1 L flask followed by $POCl_3$ with stirring added DMA over 30 minutes. An exothermic reaction takes place to a temperature of 56° C. After the exothermic reaction subsides the reaction mixture is heated to 90° C. for 1 hour and then heated to 105–115° C. for 4 hours. After 5 hours the mixture is quenched onto ice with stirring and filtered. The off gray solid is washed 2×100 mL with cold water, then air dried on filter overnight. The yield of the gray solid is 57 g. The solid is recrystallized from 500 mL heptane, treated with 2 g charcoal and filtered hot through Celite. The filtrate volume is reduced to 75 mL and filtered to yield a solid which is washed with heptane and dried on the filter. 47 g of product is obtained. The filtrate volume is reduced and solid that precipitates is filtered to yield an additional 2.8 g of product (2 crops 85%).

EXAMPLE 81

2,4-Dihydroxy-3-nitropyridine (23.7 g, 0.152 mL) is placed in a 500 mL flask, followed by $POCl_3$ (42.5 mL, 0.457 mol) with agitation. DIPEA (39.7 mL, 0.228 mol) is added over 45 minutes which results in an exothermic reaction to 67° C. After the exothermic reaction subsides the mixture is heated to 90° C. After the purity is determined to be 98.6%, the reaction mixture is quenched by adding 250 g of ice/50 ml $H_2O$. The solid is filtered, washed 2×100 mL of deionized $H_2O$ and allowed to dry on filter for 72 hours. The product yield is 25.1 g (85%) which is light tan in color.

Compounds prepared from intermediates prepared according to the process of the present invention are useful as anti-hypertensive agents for the treatment of high blood pressure; they also increase coronary blood flow, and, accordingly, are useful in the treatment of myocardial ischemia; they also act as cardioprotective agents useful for the prevention or reduction of injury to the myocardium consequent to myocardial ischemia; and they also act as antilipolytic agents useful for the treatment of hyperlipidemia and hypercholesterolemia.

Compounds prepared from intermediates prepared according to the processes of the present invention exhibit activity in standard $A_1/A_2$ receptor binding assays for the determination of adenosine receptor agonist activity in mammals. Exemplary test procedures which are useful in determining the receptor binding affinity of the compounds are described below.

A. In Vitro Adenosine Receptor Binding Affinity Determination $A_1$ Receptor Binding Affinity is determined by competition assay based on ligand displacement of $^3$H-CHA (cyclohexyl adenosine) [Research Biochemicals Inc., Natick, Mass.] from receptor using a membrane preparation of whole rat brain, according to the procedure of R. F. Bruns et al., Mol. Pharmacol., 29:331 (1986). Non-specific binding is assessed in the presence of 1 mM theophylline.

$A_2$ receptor binding affinity is determined by a similar assay technique, based on ligand displacement of $^3$H-CGS 21680, a known $A_2$ receptor-specific adenosine agonist, from receptor, using membranes from rat brain striatum. Non-specific binding is assessed in the presence of 20 μm 2-chloroadenosine.

The assays are run in glass test tubes in duplicate at 25° C. Once the membranes are added, the tubes are vortexed and incubated at 25° C. for 60 minutes ($A_1$ assay) or 90 minutes ($A_2$ assay) on a rotary shaker. The assay tubes are vortexed halfway through the incubation and again near the end. The assays are terminated by rapid filtration through 2.4 cm GF/B filters using a Brandel Cell Harvestor. The test tubes are washed three times with cold 50 mM tris-HCl (pH 7.7 or 7.4), with filtration being completed within 15 seconds. The damp filter circles are placed in glass scintillation vials filled with 10 ml of Aquasol II (New England Nuclear). The vials are allowed to shake overnight on a rotary shaker and are placed into a liquid scintillation analyzer for two minute counts. $IC_{50}$ values for receptor binding, i.e. the concentration at which a compound of Formula I displaced the radiolabeled standard, are obtained using a curve-fitting computer program (RS/1, Bolt, Beranek and Newman, Boston, Mass.).

B. In Vitro Vasorelaxation Determination in Isolated Swine Coronary Arteries Swine coronary arteries are obtained from a local slaughter house, dissected carefully and cleaned of fat, blood and adhering tissue. Rings approximately 2–3 mm wide are cut and transferred to water-jacketed tissue baths (10 mL) filled with warm (37° C.), oxygenated ($O_2/CO_2$:95%/5%) Krebs-Henseleit buffer and mounted on L-shaped hooks between stainless steel rods and a force transducer. The composition of the Krebs buffer is as follows (mM): NaCl, 118; KCl, 4.7; $CaCl_2$, 2.5; $MgSO_4$, 1.2; $KH_2PO_4$, 1.2: $NaHCO_3$, 25.0: and glucose, 10.0. Rings are equilibrated for 90 minutes with frequent buffer changes at a resting tension of 5 g. In order to assure optimal tension development, arterial rings are printed twice with 36 mM KCl and once with 10 μm. PGF2a, before being exposed to 3 μM PGF2a. When isometric tension had reached a steady state, accumulative doses of the adenosine agonists of the invention (usually 1 mM to 100 μM, in half logs) are added to the baths. Tension achieved with 3 μM PGF2a is considered equivalent to 100%; all other values are expressed as a percentage of that maximum. $IC_{50}$ values for relaxation, i.e. the concentration at which a compound of Formula I caused a 50% reduction in tension, are determined using the above-mentioned linear curve fitting computer program.

C. In Vivo Mean Arterial Blood Pressure (Map) and Heart Rate (Hr) Determinations in Normotensive Anesthetized and Spontaneously Hypertensive Rat 1. Anesthetized Rat Normotensive rats are anesthetized with sodium pentobarbital (50 mg/kg, i.p.) and placed on a heated surgical table. Cannulas are inserted into the femoral artery and veined to allow the measurement of arterial pressure and to facilitate the intravenous administration of test compounds. The animals are allowed to equilibrate for 10 minutes after surgery. Mean arterial pressure is continuously measured and recorded and heart rate is monitored using the arterial pressure pulse to trigger a cardiotachometer. After baseline parameters are established and recorded, increasing doses (1, 3, 10, 30, 100, 300 and 1000 μg/kg) of the compound of Formula I to be tested are administered intravenously. Maximal changes in the cardiovascular parameters are observed after each dose of the adenosine agonist. Only one compound is administered per rat. The potency of the compounds to lower heart rate and mean arterial pressure are assessed by determining the dose of the agent necessary to lower the heart rate or arterial pressure by 25% ($ED_{25}$).

2. Spontaneously Hypertensive Rat (SHR)

The oral antihypertensive activity of compounds of Formula I are examined in conscious spontaneously hypertensive rats. The rats are anesthetized with sodium phenobarbitol (50 mg/kg i.p.). A telemetry transducer is implanted into the rats abdomen via midline incision. The cannula of the transducer is inserted into the abdominal aorta to allow direct measurement of arterial pressure in the conscious SHR. The transducer is secured to the abdominal wall. After recovery from surgery (minimum of seven days), the SHR are placed on a receiver plate and the transducer/transmitter is activated. Systolic diastolic and mean arterial pressure and heart rate are recorded for 1.5 hours in the unrestrained conscious rat to establish a stable baseline. Each rat then received a single dose of the compound of Formula I to be tested or vehicle, and changes in arterial pressure and heart rate are monitored for 20 hours and recorded.

Table II presents results of the biological activity determinations for exemplary compounds, and for the compound of Example 6, Step 1, within the scope of compounds of Formula I.

tective activity of myocardial preconditioning. Exemplary test procedures which are useful in determining the cardioprotective activity of compounds of Formula I are described below.

TABLE II

| Ex. No. | Adenosine Receptor Binding Activity/ $IC_{50}$ (nM) HR/% $A_1$ | $A_2$ | Vasorelaxation in Swine Coronary Artery/ $IC_{50}$ ($\mu$M) | Blood Press/Heart Rate | | | | |
|---|---|---|---|---|---|---|---|---|
| | | | | Anesthetized Rat | | SHR* | | |
| | | | | MAP/$ED_{25}$ ($\mu$g/kg) | HR/$ED_{25}$ ($\mu$g/kg) | Dose (mg/kg) | MAP/% | |
| 4 | 1.66 | 55 | 0.73 | 13 | 19 | 5 | 28(D) | 20(D) |
| 5 | 4.26 | 91 | 0.068 | — | — | — | — | — |
| 6 | 2.69 | 12.88 | 0.021 | — | — | 1 | 18(D) | 7(I) |
| 6(1) | >1000 | >1000 | 19.1 | — | — | — | — | — |
| 7 | 3.5 | 28 | 4 | 6 | 18 | 5 | 45(D) | 22(D) |
| 8 | 5 | 138 | — | 10 | 23 | — | — | — |
| 9 | 4 | 1000 | 11.9 | 5 | 4 | — | — | — |
| 10 | 3.8 | >1000 | — | — | — | — | — | — |
| 11 | 7.4 | >1000 | — | — | — | — | — | — |
| 12 | 23 | 224 | 0.5 | 4 | 17 | — | — | — |
| 13 | 41 | 191 | 0.24 | 3 | >10 | — | — | — |
| 14 | 79.4 | >1000 | — | — | — | — | — | — |
| 15 | 4.07 | 1000 | 2.45 | 1.5 | 1.4 | — | — | — |
| 16 | 1.7 | >1000 | — | — | — | — | — | — |
| 17 | 67.6 | 5248 | 18.77 | — | — | — | — | — |
| 18 | 166 | 52 | 0.46 | 2 | >10 | — | — | — |
| 19 | 36 | 1000 | 0.75 | — | — | — | — | — |
| 20 | 3.98 | 158 | — | — | — | — | — | — |
| 21 | 0.09 | 14.8 | — | — | — | — | — | — |
| 22 | 2.69 | 29.5 | 0.1 | — | — | — | — | — |
| 23 | 0.32 | 891 | 4.4 | 6 | 7 | — | — | — |
| 24 | >1000 | >1000 | — | 6 | >10 | 5 | 17(D) | 6(I) |
| 25 | 1258.3 | 355 | 0.64 | — | — | — | — | — |
| 26 | 87.1 | 63.1 | 0.082 | 4 | >30 | 2.5 | 41(D) | 3(I) |
| 27 | 5.01 | 29.5 | 0.043 | — | — | 1 | 27 (D) | 1(I) |
| 28 | 417 | >1000 | — | — | — | — | — | — |
| 29 | 35.48 | >1000 | 22 | 16 | 31 | 5 | 18(D) | 2(D) |
| 30 | 562 | >1000 | 12.1 | 6 | >10 | — | — | — |
| 31 | 0.03 | 8.9 | — | — | — | — | — | — |
| 32 | 0.049 | 45 | — | — | — | — | — | — |
| 34 | 1.6 | 23 | 0.072 | — | — | — | — | — |
| 35 | 1087 | 6351 | 3.3 | — | — | — | — | — |
| 36 | 8.8 | 43.4 | 0.493 | — | — | — | — | — |
| 37 | 16.2 | 110 | 0.45 | — | — | — | — | — |
| 38 | 5.7 | 55.5 | 0.47 | — | — | — | — | — |
| 39 | 3.98 | 46.8 | — | — | — | — | — | — |
| 40 | 9.3 | 68.8 | 283 | — | — | — | — | — |
| 41 | 14.2 | 158 | — | — | — | — | — | — |
| 42 | >1000 | >10000 | 2.44 | — | — | — | — | — |
| 43 | 8428 | >1000 | 7.83 | — | — | — | — | — |
| 44 | 55 | 331 | 0.316 | — | — | — | — | — |
| 45 | 6351 | >10000 | 4.1 | — | — | — | — | — |
| 46 | 13.5 | 81 | 3.52 | — | — | — | — | — |
| 47 | 23 | 2818 | 5.7 | — | — | — | — | — |
| 48 | 8.35 | 1445 | — | — | — | — | — | — |
| 49 | 69 | 2884 | 9.81 | — | — | — | — | — |

*D signifies decrease; I signifies increase

When the blood flow to the heart is interrupted for brief periods of time (2 to 5 minutes), followed by restoration of blood flow (reperfusion), the heart becomes protected against the development of injury when the blood flow is interrupted for longer periods of time (for example, 30 minutes).

Compounds of Formula I exhibit activity in tests used to determine the ability of compounds to mimic the cardiopro- Determination of Cardioprotective Activity in Rat 1. General Surgical Preparation Adult Sprague-Dawley rats are anesthetized with Inactin (100 mg/kg i.p.). The trachea is intubated and positive pressure ventilation is provided via a small animal respirator. Catheters are placed in the femoral vein and artery for administration of compounds of the present invention to be tested, and measurement of blood pressure, respectively. An incision is made on the left side of the thorax over the pectoral muscles, and the muscles are retracted to expose the fourth intercostal space. The chest cavity is opened and the heart is exposed. A length of 4-0 proline suture is placed through the ventricular wall near the left main coronary artery and is used to interrupt blood flow through the coronary artery by tightening a slip-knot. A pulsed-Doppler flow probe (a device which measures blood flow) is placed on the surface of the heart to confirm that the coronary artery has been properly identified. A catheter is also placed in the left ventricle to monitor left ventricular function during the experiment 2. Preconditioning and Test Procedures For preconditioning the heart, the coronary artery is occluded (flow is interrupted) for a period of two minutes. The slip-knot is then released to restore flow (reperfusion) for a period of three minutes. This procedure of occlusion/reperfusion is repeated twice. Five minutes after completion of the final preconditioning event the artery is reoccluded for 30 minutes, followed by reperfusion for three hours. When a compound of Formula I is being tested, instead of performing the occlusion/reperfusion procedure, the compound is infused for 30 minutes prior to the 30-minute occlusion period. At the conclusion of the 3-hour reperfusion period the artery is reoccluded and 1 ml of Patent Blue dye is administered into the left ventricular catheter and the heart is stopped by i.v. administration of potassium chloride. This procedure allows the dye to perfuse the normal areas of the heart while that portion of the heart that is made ischemic does not take up the dye (this is the area at risk, the "risk area"). The heart is quickly removed for analysis of infarct size. Infarct size is determined by slicing the heart from apex to base into four to five slices 1–2 mm thick. Slices are incubated in a solution of 1% triphenytltetrazolium for 15 minutes. This stain reacts with viable tissue and causes it to develop a brick-red color. The infarcted tissue does not react with the stain and is pale white in appearance. The tissue slices are placed in a video image analysis system and infarct size is determined by planimetry. The effect of the compound of the present invention tested on myocardial infarct size is assessed and used to quantitate the extent of cardioprotective activity. Results are given as the percentage of the risk area which is infarcted.

Results of testing of an exemplary compounds of Formula I by the above methods are given in Table III below.

TABLE III

| Animal Group | % Risk Area Infarcted |
| --- | --- |
| Control[1] | 63 ± 5 |
| Preconditioned[2] | 15 ± 8 |
| Compound Low[3] | 23 ± 9 |
| Compound High[4] | 18 ± 5 |

[1]Animals not preconditioned or treated with compound.
[2]Animals preconditioned by occlusion/reperfusion procedure.
[3]Animals received i.v. bolus of 1 µg/kg, followed by i.v. infusion of 0.1 µg/kg/minute for 30 minutes prior to 30 minute occlusion period, of Compound of Example 39.
[4]Animals received i.v. bolus of 10 µg/kg, followed by i.v. infusion of 1 µg/kg/minute for from 30 minutes prior to 30 minute occlusion period to 2 hours after initiation of reperfusion, of Compound of Example 39.

Compounds of Formula I exhibit activity in tests used to determine the ability of compounds to inhibit lipolysis. Exemplary test procedures which are useful in determining the antipolytic activity of compounds of Formula I are described below.

Determination of Antilipolytic Activity in Rat Adipocytes

1. Isolation of Adipocytes from Epididymal Fat Pads

Adipose tissue is removed from anesthetized rats and rinsed twice in incubation medium (2.09 g sodium bicarbonate and 0.04 g EDTA, disodium salt, in 1 L Krebs buffer). Each rat (300–350 g) yields approximately 4 ml of adipose tissue. The adipose tissue (35 mL) is cut into small pieces with scissors and washed with incubation medium (50 mL). The mixture is poured into the barrel of a 50 mL syringe to which is attached a short piece of clamped tubing instead of a needle. The aqueous phase is allowed to drain. A second wash with incubation medium is passed through the syringe. The tissue is added to 50 mL of collagenase solution (collagenase (90 mg), bovine serum albumin (BSA) (500 mg), and 0.1 M calcium chloride solution (1 mL), in incubation medium (50 mL)) in a 1 L bottle. The mixture is shaken in an environmental at 37° C. for about 60 minutes under an atmosphere of 95% oxygen/5% carbon dioxide to effect digestion of the tissue. The dispersed cells are poured through 2 layers of cheese cloth into a 100 mL plastic beaker. The undigested clumps in the cloth are rinsed once with incubation medium (20 mL). The cells in the beaker are centrifuged in 2 plastic tubes for 30 seconds at room temperature at 300 rpm. The aqueous phase is aspirated from beneath the loosely packed layer of floating fat cells and discarded. The adipocytes are gently poured into a 250 mL plastic beaker containing 100 mL of rinse solution (1 g BSA per 100 mL incubation medium). After gentle stirring the centrifugation step is repeated. Another wash with rinse solution follows. The cells are pooled and their volume is estimated with a graduated cylinder. The adipocytes are diluted in twice their volume of assay buffer (incubation medium (120 mL). BSA (1.2 g), pyruvic acid (13 mg)).

2. In Vitro Lipolysis Assay

The assay is performed in 20 mL plastic scintillation vials and the total assay volume is 4.2 ml. Assay buffer (2.5 mL), diluted adipocytes (1.5 mL), and a solution of the compound to be tested (12.3 µL) adenosine agonist (12.3 µL; varying concentration) is incubated in the environmental shaker for 15 minutes, then the reaction is started with norepinephrine solution (41.2 µL) (10 nM, in a carrier solution containing water (100 mL), BSA (4 mg), and 0.1 M EDTA (20 µL))and adenosine deaminase (1 µg/ml, 41.2 µL). After sixty minutes in the shaker the reaction is terminated by putting the vials on ice. The contents of each vial is transferred into a 12×75 mm glass tube and centrifuged at 8–10° C. at 3600 rpm for 20 minutes. The hard lipid layer is removed by aspiration and the aqueous layer is assayed for glycerol (400 µL of sample). The positive control is done in the absence of any adenosine agonist, substituting water in place of the solution to be tested.

Results of testing compounds of Formula I are given in Table IV, below, and are reported as the % inhibition of glycerol production of 1 µM and/or 0.1 µM of compound tested versus the positive control and as $EC_{50}$ values, i.e., the concentration of compound tested necessary to effect a 50% inhibition of glycerol production. For purposes of comparison, results are also given for literature compounds N-cyclopentyladenosine (CPA), N-ethylcarboxamidoadenosine (NECA), R-phenylisopropyladenosine (R-PIA), and 2-[[2-[4-[2-carboxethyl)phenyl]ethyl]amino]-N-ethylcarboxamidoadenosine (CGS21680).

TABLE IV

| Compound Example No. | 1 µM | % Inhibition 0.1 µM | $EC_{50}$ |
|---|---|---|---|
| 6 | | | 0.76 nM |
| 26 | 96 | | 89 nM |
| 31 | | | 0.26 pM |
| 39 | | | 5.4 nM |
| 41 | | 88 | |
| 46 | | | 4 nM |
| 47 | | 94 | 0.63 nM |
| 48 | | 88 | 1.86 nM |
| 49 | | 85 | 18.6 nM |
| CPA | 100 | 97 | 0.31 nM |
| NECA | | | 2.5 nM |
| R-PIA | | | 1 nM |
| CGS21680 | 0 | | |

The $A_1$ and $A_2$ adenosine receptor binding and vasorelation activity for the literature compounds in Table IV, as determined by the methods described hereinabove, are given in Table V, below.

TABLE V

| Compound | Adenosine Receptor Binding ($IC_{50}$) | | Vasorelaxation ($IC_{50}$) |
|---|---|---|---|
| | $A_1$ (nM) | $A_2$ (nM) | |
| CPA | 0.72 | 1584 | 3.18 |
| NECA | 12 | 17 | 0.017 |
| R-PIA | 2.4 | 300 | 0.76 |
| CGS21680 | 30000 | 70 | 0.08 |

The antilipolytic activity of adenosine is mediated through activation of the $A_1$ receptor subtype. Selective agonists of the $A_2$ receptor subtype, such as CGS 21680, do not exhibit antilipolytic activity. Accordingly, while certain $A_1$ selective agonist may not have desirable antihypertensive activity and $A_2$ agonists may not be effective antilipolytic agents, compounds of the present invention which are mixed agonists are uniquely suited to effectively treat both risk factors discussed hereinabove, i.e., hypertension and hyperlipidemia.

The compounds of Formula I can be normally administered orally or parenterally, in the treatment of patients suffering from hypertension, myocardial ischemia, or in patients in need of cardioprotective therapy or antilipolytic therapy. As used herein, the term "patients" includes humans and other mammals.

The compounds of Formula I, preferably in the form of a salt, may be formulated for administration in any convenient way, and the invention includes within its scope pharmaceutical compositions containing at least one compound of Formula I adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserning agents, in order to provide a pharmaceutically acceptable preparation.

The particular carrier and the ratio of the adenosine agonists to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated. The carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for administration by intramuscular and subcutaneous injection. The aqueous solutions, including those of the salts dissolved in pure distilled water, are suitable for administration by intravenous injection, provided that their pH is properly adjusted, and that they are suitably buffered, made isotonic with sufficient saline or glucose and sterilized by heating or by microfiltration.

The dosage regimen is that which insures maximum therapeutic response until improvement is obtained and thereafter the minimum effective level which gives relief. Thus, in general, the dosages are those that are therapeutically effective in lowering blood pressure in the treatment of hypertension, in increasing coronary blood flow in the treatment of myocardial ischemia, in producing a cardioprotective effect, i.e., amelioration of ischemic injury or myocardial infarct size consequent to myocardial ischemia, or in producing an antilipolytic effect. In general, the oral dose may be between about 0.1 and about 100 (preferably in the range of 1 to 10 mg/kg), and the i.v. dose about 0.01 to about 10 mg/kg (preferably in the range of 0.1 to 5 mg/kg), bearing in mind, of course, that in selecting the appropriate dosage in any specific case, consideration must be given to the patient's weight general health, age and other factors which may influence response to the drug.

The compounds of Formula I may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally about 1 to about 4 times per day. It is anticipated that many patients will require no more than about one to about two doses daily.

It is also anticipated that the compounds of Formula I would be useful as an injectable dosage form which may be administered in an emergency to a patient suffering from acute hypertension or myocardial ischemia, or a patient in need of cardioprotection or antilipolytic therapy. Such treatment may be followed by intravenous infusion of the active compound and the amount of compound infused into such a patient should be effective to achieve and maintain the desired therapeutic response.

What is claimed is:

1. A process for preparing 2,4-dihydroxypyridine comprising heating a compound of the formula A

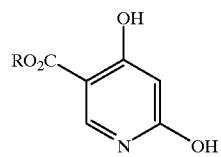

(A)

wherein R is H, alkyl or aralkyl and phosphoric acid where the ratio of phosphoric acid to water is not less than about 27 to 1 weight %.

2. The process according to claim 1 wherein the ratio is obtained by removing water therefrom.

3. The process according to claim 2 wherein the removal is effected by distillation.

4. The process according to claim 1 wherein the phosphoric acid and the compound of formula A is heated to about 210° C.

* * * * *